(12) United States Patent
Anex et al.

(10) Patent No.: US 8,794,929 B2
(45) Date of Patent: Aug. 5, 2014

(54) ELECTROKINETIC PUMP DESIGNS AND DRUG DELIVERY SYSTEMS

(75) Inventors: Deon Stafford Anex, Livermore, CA (US); Charles Martin Schwimmer, Los Gatos, CA (US); David Laurence Black, Los Gatos, CA (US); Richard Dean Rush, Belmont, CA (US); Michael James Gearhart, Fremont, CA (US)

(73) Assignee: Eksigent Technologies LLC, Dublin, CA (US)

( * ) Notice: Subject to any disclaimer, the term of this patent is extended or adjusted under 35 U.S.C. 154(b) by 253 days.

(21) Appl. No.: 11/603,925

(22) Filed: Nov. 22, 2006

(65) Prior Publication Data

US 2007/0148014 A1    Jun. 28, 2007

Related U.S. Application Data

(60) Provisional application No. 60/739,390, filed on Nov. 23, 2005.

(51) Int. Cl.
*F04B 37/02* (2006.01)

(52) U.S. Cl.
USPC .............................................. 417/48; 417/49

(58) Field of Classification Search
USPC ........................... 417/48, 390, 49; 604/892.1
See application file for complete search history.

(56) References Cited

U.S. PATENT DOCUMENTS

| | | | |
|---|---|---|---|
| 1,063,204 A | 6/1913 | Kraft | |
| 2,615,940 A | 10/1952 | Williams | |
| 2,644,900 A | 7/1953 | Hardway, Jr. | |
| 2,644,902 A | 7/1953 | Hardway, Jr. | |
| 2,661,430 A | 12/1953 | Hardway, Jr. | |
| 2,841,324 A * | 7/1958 | Santeler | 417/49 |
| 2,995,714 A | 8/1961 | Hannah | |
| 3,143,691 A | 8/1964 | Hurd | |
| 3,209,255 A | 9/1965 | Estes et al. | |
| 3,298,789 A | 1/1967 | Mast | |

(Continued)

FOREIGN PATENT DOCUMENTS

| | | |
|---|---|---|
| CN | 2286429 Y | 7/1998 |
| DE | 1817719 A1 | 7/1970 |

(Continued)

OTHER PUBLICATIONS

PCT/US2006/045313, International Preliminary Report on Patentability and Written Opinion dated Sep. 13, 2007.

(Continued)

*Primary Examiner* — Christopher Bobish
(74) *Attorney, Agent, or Firm* — Shay Glenn LLP

(57) ABSTRACT

The present invention provides a fluid delivery system having a first chamber, a second chamber and a third chamber; a flow-through pump element separating the first chamber from the second chamber; a moveable pump element separating the second chamber from the third chamber; a first outlet in communication with the third chamber; and second outlet in communication with the second chamber. Additionally, the present invention provides methods of operating a fluid delivery system having a first chamber, a second chamber and a delivery chamber by reducing the volume of the second chamber while increasing the volume of the delivery chamber without operation of a flow-through pump element that separates the second chamber from the first chamber.

14 Claims, 12 Drawing Sheets

(56) References Cited

U.S. PATENT DOCUMENTS

| | | | |
|---|---|---|---|
| 3,427,978 A | 2/1969 | Hanneman et al. | |
| 3,544,237 A | 12/1970 | Walz | |
| 3,587,227 A | 6/1971 | Weingarten et al. | |
| 3,604,417 A * | 9/1971 | Stolzenberg | 604/131 |
| 3,630,957 A | 12/1971 | Rey et al. | |
| 3,666,379 A | 5/1972 | Mitchel et al. | |
| 3,682,239 A | 8/1972 | Abu-Romia | |
| 3,714,528 A | 1/1973 | Vail | |
| 3,739,573 A | 6/1973 | Giner | |
| 3,923,426 A | 12/1975 | Theeuwes | |
| 3,952,577 A | 4/1976 | Hayes et al. | |
| 4,043,895 A * | 8/1977 | Gritzner | 204/600 |
| 4,140,122 A | 2/1979 | Kuhl et al. | |
| 4,209,014 A | 6/1980 | Sefton | |
| 4,240,889 A | 12/1980 | Yoda et al. | |
| 4,316,233 A | 2/1982 | Chato et al. | |
| 4,383,265 A | 5/1983 | Kohashi | |
| 4,396,925 A | 8/1983 | Kohashi | |
| 4,402,817 A | 9/1983 | Maget | |
| 4,552,277 A | 11/1985 | Richardson et al. | |
| 4,634,431 A | 1/1987 | Whitney et al. | |
| 4,639,244 A | 1/1987 | Rizk et al. | |
| 4,687,424 A | 8/1987 | Heimes | |
| 4,704,324 A | 11/1987 | Davis et al. | |
| 4,789,801 A | 12/1988 | Lee | |
| 4,808,152 A | 2/1989 | Sibalis | |
| 4,886,514 A | 12/1989 | Maget | |
| 4,902,278 A * | 2/1990 | Maget et al. | 604/132 |
| 4,908,112 A | 3/1990 | Pace | |
| 4,921,041 A | 5/1990 | Akachi | |
| 4,999,069 A | 3/1991 | Brackett et al. | |
| 5,004,543 A | 4/1991 | Pluskal et al. | |
| 5,037,457 A | 8/1991 | Goldsmith et al. | |
| 5,087,338 A | 2/1992 | Perry et al. | |
| 5,116,471 A | 5/1992 | Chien et al. | |
| 5,126,022 A | 6/1992 | Soane et al. | |
| 5,137,633 A | 8/1992 | Wang | |
| 5,219,020 A | 6/1993 | Akachi | |
| 5,260,855 A | 11/1993 | Kaschmitter et al. | |
| 5,279,608 A * | 1/1994 | Cherif Cheikh | 604/892.1 |
| 5,288,214 A | 2/1994 | Fukuda et al. | |
| 5,296,115 A | 3/1994 | Rocklin et al. | |
| 5,312,389 A * | 5/1994 | Theeuwes et al. | 604/892.1 |
| 5,351,164 A | 9/1994 | Grigortchak et al. | |
| 5,418,079 A | 5/1995 | Diethelm | |
| 5,523,177 A | 6/1996 | Kosek et al. | |
| 5,531,575 A | 7/1996 | Lin | |
| 5,534,328 A | 7/1996 | Ashmead et al. | |
| 5,573,651 A | 11/1996 | Dasgupta et al. | |
| 5,581,438 A | 12/1996 | Halliop | |
| 5,628,890 A | 5/1997 | Carter et al. | |
| 5,632,876 A | 5/1997 | Zanzucchi et al. | |
| 5,658,355 A | 8/1997 | Cottevieille et al. | |
| 5,683,443 A | 11/1997 | Munshi et al. | |
| 5,766,435 A | 6/1998 | Liao et al. | |
| 5,858,193 A | 1/1999 | Zanzucchi et al. | |
| 5,862,035 A | 1/1999 | Farahmandi et al. | |
| 5,888,390 A | 3/1999 | Craig | |
| 5,891,097 A | 4/1999 | Saito et al. | |
| 5,942,093 A | 8/1999 | Rakestraw et al. | |
| 5,942,443 A | 8/1999 | Parce et al. | |
| 5,958,203 A | 9/1999 | Parce et al. | |
| RE36,350 E | 10/1999 | Swedberg et al. | |
| 5,961,800 A | 10/1999 | McBride et al. | |
| 5,964,997 A | 10/1999 | McBride | |
| 5,989,402 A | 11/1999 | Chow et al. | |
| 5,997,708 A | 12/1999 | Craig | |
| 6,007,690 A | 12/1999 | Nelson et al. | |
| 6,012,902 A | 1/2000 | Parce | |
| 6,013,164 A | 1/2000 | Paul et al. | |
| 6,019,745 A | 2/2000 | Gray | |
| 6,019,882 A | 2/2000 | Paul et al. | |
| 6,045,933 A | 4/2000 | Okamoto | |
| 6,054,034 A | 4/2000 | Soane et al. | |
| 6,068,243 A | 5/2000 | Hoggan | |
| 6,068,752 A | 5/2000 | Dubrow et al. | |
| 6,068,767 A | 5/2000 | Garguilo et al. | |
| 6,074,725 A | 6/2000 | Kennedy | |
| 6,086,243 A | 7/2000 | Paul et al. | |
| 6,090,251 A | 7/2000 | Sundberg et al. | |
| 6,100,107 A | 8/2000 | Lei et al. | |
| 6,106,685 A | 8/2000 | McBride et al. | |
| 6,113,766 A | 9/2000 | Steiner et al. | |
| 6,126,723 A | 10/2000 | Drost et al. | |
| 6,129,973 A | 10/2000 | Martin et al. | |
| 6,137,501 A | 10/2000 | Wen et al. | |
| 6,150,089 A | 11/2000 | Schwartz | |
| 6,156,273 A | 12/2000 | Regnier et al. | |
| 6,159,353 A | 12/2000 | West et al. | |
| 6,167,910 B1 | 1/2001 | Chow | |
| 6,176,962 B1 | 1/2001 | Soane et al. | |
| 6,179,586 B1 | 1/2001 | Herb et al. | |
| 6,210,986 B1 | 4/2001 | Arnold et al. | |
| 6,224,728 B1 | 5/2001 | Oborny et al. | |
| 6,238,538 B1 | 5/2001 | Parce et al. | |
| 6,255,551 B1 | 7/2001 | Shapiro et al. | |
| 6,257,844 B1 | 7/2001 | Stern | |
| 6,260,579 B1 | 7/2001 | Yokota et al. | |
| 6,267,858 B1 | 7/2001 | Parce et al. | |
| 6,274,089 B1 | 8/2001 | Chow et al. | |
| 6,277,257 B1 | 8/2001 | Paul et al. | |
| 6,287,438 B1 | 9/2001 | Knoll | |
| 6,287,440 B1 | 9/2001 | Arnold et al. | |
| 6,290,909 B1 | 9/2001 | Paul et al. | |
| 6,319,476 B1 | 11/2001 | Victor, Jr. et al. | |
| 6,320,160 B1 | 11/2001 | Eidsnes et al. | |
| 6,344,120 B1 | 2/2002 | Haswell et al. | |
| 6,349,740 B1 | 2/2002 | Cho et al. | |
| 6,379,402 B1 | 4/2002 | Suhara et al. | |
| 6,406,605 B1 | 6/2002 | Moles | |
| 6,409,698 B1 | 6/2002 | Robinson et al. | |
| 6,418,966 B2 | 7/2002 | Loo | |
| 6,418,968 B1 | 7/2002 | Pezzuto et al. | |
| 6,444,150 B1 | 9/2002 | Arnold | |
| 6,460,420 B1 | 10/2002 | Paul et al. | |
| 6,472,443 B1 | 10/2002 | Shepodd | |
| 6,477,410 B1 | 11/2002 | Henley et al. | |
| 6,495,015 B1 | 12/2002 | Schoeniger et al. | |
| 6,529,377 B1 | 3/2003 | Nelson et al. | |
| 6,561,208 B1 | 5/2003 | O'Connor et al. | |
| 6,572,823 B1 | 6/2003 | Donahue et al. | |
| 6,605,472 B1 | 8/2003 | Skinner et al. | |
| 6,613,211 B1 | 9/2003 | McCormick et al. | |
| 6,619,925 B2 | 9/2003 | Ohkawa | |
| 6,620,625 B2 | 9/2003 | Wolk et al. | |
| 6,655,923 B1 | 12/2003 | Lisec et al. | |
| 6,685,442 B2 | 2/2004 | Chinn et al. | |
| 6,689,373 B2 | 2/2004 | Johnson et al. | |
| 6,709,559 B2 | 3/2004 | Sundberg et al. | |
| 6,719,535 B2 | 4/2004 | Rakestraw et al. | |
| 6,729,352 B2 | 5/2004 | O'Connor et al. | |
| 6,733,244 B1 | 5/2004 | Fritsch et al. | |
| 6,766,817 B2 | 7/2004 | da Silva | |
| 6,770,182 B1 | 8/2004 | Griffiths et al. | |
| 6,770,183 B1 | 8/2004 | Hencken et al. | |
| 6,814,859 B2 | 11/2004 | Koehler et al. | |
| 6,832,787 B1 | 12/2004 | Renzi | |
| 6,843,272 B2 | 1/2005 | Schoeniger et al. | |
| 6,872,292 B2 | 3/2005 | Theeuwes et al. | |
| 6,878,473 B2 | 4/2005 | Yamauchi et al. | |
| 6,881,312 B2 | 4/2005 | Kopf-Sill et al. | |
| 6,905,583 B2 | 6/2005 | Wainright et al. | |
| 6,918,404 B2 | 7/2005 | Dias da Silva | |
| 6,942,018 B2 | 9/2005 | Goodson et al. | |
| 6,952,962 B2 | 10/2005 | Hasselbrink et al. | |
| 6,962,658 B2 | 11/2005 | Neyer et al. | |
| 6,994,151 B2 | 2/2006 | Zhou et al. | |
| 7,050,660 B2 | 5/2006 | Cyr et al. | |
| 7,094,464 B2 | 8/2006 | Mao et al. | |
| 7,101,947 B2 | 9/2006 | Schlenoff et al. | |
| 7,147,955 B2 | 12/2006 | Adams | |
| 7,207,982 B2 * | 4/2007 | Dionne et al. | 604/892.1 |
| 7,217,351 B2 * | 5/2007 | Krumme | 204/600 |
| 7,231,839 B2 | 6/2007 | Huber et al. | |

(56) References Cited

U.S. PATENT DOCUMENTS

| | | | |
|---|---|---|---|
| 7,235,164 B2 | 6/2007 | Anex et al. | |
| 7,258,777 B2 | 8/2007 | Paul et al. | |
| 7,267,753 B2 | 9/2007 | Anex et al. | |
| 7,364,647 B2 | 4/2008 | Paul et al. | |
| 7,371,229 B2 | 5/2008 | Theeuwes et al. | |
| 7,399,398 B2 | 7/2008 | Rakestraw et al. | |
| 7,429,317 B2 | 9/2008 | Paul | |
| 7,470,267 B2 * | 12/2008 | Joshi et al. | 604/892.1 |
| 7,517,440 B2 | 4/2009 | Anex et al. | |
| 7,521,140 B2 | 4/2009 | Arnold et al. | |
| 7,559,356 B2 | 7/2009 | Paul et al. | |
| 7,575,722 B2 | 8/2009 | Arnold | |
| 7,898,742 B2 | 3/2011 | Rodriguez Fernandez et al. | |
| 2001/0008212 A1 | 7/2001 | Shepodd et al. | |
| 2001/0052460 A1 | 12/2001 | Chien et al. | |
| 2002/0043805 A1 | 4/2002 | Charles et al. | |
| 2002/0048425 A1 | 4/2002 | McBride et al. | |
| 2002/0056639 A1 | 5/2002 | Lackritz et al. | |
| 2002/0066639 A1 | 6/2002 | Taylor et al. | |
| 2002/0070116 A1 | 6/2002 | Ohkawa | |
| 2002/0076598 A1 | 6/2002 | Bostaph et al. | |
| 2002/0089807 A1 | 7/2002 | Bluvstein et al. | |
| 2002/0125134 A1 | 9/2002 | Santiago et al. | |
| 2002/0166592 A1 | 11/2002 | Liu et al. | |
| 2002/0187074 A1 | 12/2002 | O'Connor et al. | |
| 2002/0187197 A1 | 12/2002 | Caruso et al. | |
| 2002/0187557 A1 | 12/2002 | Hobbs et al. | |
| 2002/0189947 A1 | 12/2002 | Paul et al. | |
| 2002/0195344 A1 | 12/2002 | Neyer et al. | |
| 2003/0044669 A1 | 3/2003 | Hidaka et al. | |
| 2003/0052007 A1 | 3/2003 | Paul et al. | |
| 2003/0061687 A1 | 4/2003 | Hansen et al. | |
| 2003/0114837 A1 * | 6/2003 | Peterson et al. | 604/892.1 |
| 2003/0116738 A1 | 6/2003 | O'Connor et al. | |
| 2003/0138678 A1 | 7/2003 | Preidel | |
| 2003/0173781 A1 | 9/2003 | Dodgson et al. | |
| 2003/0190514 A1 | 10/2003 | Okada et al. | |
| 2003/0198130 A1 | 10/2003 | Karp et al. | |
| 2003/0198576 A1 | 10/2003 | Coyne et al. | |
| 2003/0205582 A1 * | 11/2003 | Joshi et al. | 222/100 |
| 2003/0206806 A1 | 11/2003 | Paul et al. | |
| 2003/0215686 A1 | 11/2003 | DeFilippis et al. | |
| 2003/0226754 A1 | 12/2003 | Le Febre | |
| 2003/0232203 A1 | 12/2003 | Mutlu et al. | |
| 2004/0011648 A1 | 1/2004 | Paul et al. | |
| 2004/0070116 A1 | 4/2004 | Kaiser et al. | |
| 2004/0087033 A1 | 5/2004 | Schembri | |
| 2004/0101421 A1 | 5/2004 | Kenny et al. | |
| 2004/0106192 A1 | 6/2004 | Jeon et al. | |
| 2004/0115731 A1 | 6/2004 | Hansen et al. | |
| 2004/0118189 A1 | 6/2004 | Karp et al. | |
| 2004/0129568 A1 | 7/2004 | Seul et al. | |
| 2004/0163957 A1 | 8/2004 | Neyer et al. | |
| 2004/0238052 A1 | 12/2004 | Karp et al. | |
| 2004/0241004 A1 | 12/2004 | Goodson et al. | |
| 2004/0241006 A1 | 12/2004 | Taboryski et al. | |
| 2004/0247450 A1 | 12/2004 | Kutchinsky et al. | |
| 2004/0248167 A1 | 12/2004 | Quake et al. | |
| 2005/0014134 A1 | 1/2005 | West et al. | |
| 2005/0161326 A1 | 7/2005 | Morita et al. | |
| 2005/0166980 A1 | 8/2005 | Unger et al. | |
| 2005/0235733 A1 | 10/2005 | Holst et al. | |
| 2005/0252772 A1 | 11/2005 | Paul et al. | |
| 2006/0127238 A1 | 6/2006 | Mosier et al. | |
| 2006/0266650 A1 | 11/2006 | Han et al. | |
| 2007/0062250 A1 | 3/2007 | Krulevitch et al. | |
| 2007/0062251 A1 | 3/2007 | Anex | |
| 2007/0066939 A1 | 3/2007 | Krulevitch et al. | |
| 2007/0066940 A1 | 3/2007 | Karunaratne et al. | |
| 2007/0093752 A1 | 4/2007 | Zhao et al. | |
| 2007/0093753 A1 | 4/2007 | Krulevitch et al. | |
| 2007/0129792 A1 | 6/2007 | Picart et al. | |
| 2007/0144909 A1 | 6/2007 | Anex et al. | |
| 2007/0224055 A1 | 9/2007 | Anex et al. | |
| 2008/0033338 A1 | 2/2008 | Smith | |
| 2008/0173545 A1 | 7/2008 | Anex et al. | |
| 2008/0179188 A1 | 7/2008 | Nelson et al. | |
| 2009/0036867 A1 | 2/2009 | Glejboel et al. | |
| 2009/0148308 A1 | 6/2009 | Saleki et al. | |
| 2009/0185916 A1 | 7/2009 | Anex et al. | |
| 2009/0308752 A1 * | 12/2009 | Evans et al. | 204/630 |
| 2010/0096266 A1 | 4/2010 | Kim et al. | |
| 2011/0114492 A1 | 5/2011 | Anex et al. | |
| 2012/0219430 A1 | 8/2012 | Anex et al. | |
| 2012/0282111 A1 | 11/2012 | Nip et al. | |
| 2012/0282112 A1 | 11/2012 | Nip et al. | |
| 2012/0282113 A1 | 11/2012 | Anex | |
| 2013/0085462 A1 | 4/2013 | Nip et al. | |
| 2013/0156608 A1 | 6/2013 | Anex et al. | |

FOREIGN PATENT DOCUMENTS

| | | |
|---|---|---|
| EP | 0178601 A2 | 4/1986 |
| EP | 0421234 A2 | 4/1991 |
| EP | 1063204 A2 | 12/2000 |
| JP | H02-229531 | 9/1990 |
| JP | 03-08759 A | 4/1991 |
| JP | U04-034468 | 3/1992 |
| JP | 07269971 A | 10/1995 |
| JP | 09270265 A | 10/1997 |
| JP | 02-265598 | 9/2002 |
| RU | 2008147087 | 6/2010 |
| SU | 619189 A | 8/1978 |
| WO | WO 94/05354 A1 | 3/1994 |
| WO | WO 96/39252 A1 | 12/1996 |
| WO | WO 98/25065 A1 | 6/1998 |
| WO | WO 98/33001 A1 | 7/1998 |
| WO | WO 99/16162 A1 | 4/1999 |
| WO | WO 00/04832 A1 | 2/2000 |
| WO | WO 00/52376 A1 | 9/2000 |
| WO | WO 00/55502 A1 | 9/2000 |
| WO | WO 00/79131 A1 | 12/2000 |
| WO | WO 01/25138 A1 | 4/2001 |
| WO | WO 01/86155 A1 | 11/2001 |
| WO | WO 02/068821 A2 | 9/2002 |
| WO | WO02/070942 A1 | 9/2002 |
| WO | WO 02/086332 A1 | 10/2002 |
| WO | WO 2004/007348 A1 | 1/2004 |
| WO | WO2007062068 A3 | 5/2007 |
| WO | WO2007062182 A2 | 5/2007 |

OTHER PUBLICATIONS

PCT/US06/45112, International Search Report and Written Opinion dated Jan. 18, 2008.

Conway, B.E.; Electrochemical Capacitors Their Nature, Function, and Applications; Electrochemistry Encyclopedia. 2003. (Available at http://electrochem.cwru.edu/ed/encycl/art-c03-elchem-cap.htm. Accessed May 16, 2006).

Li et al., Studies on preparation and performances of carbon aerogel electrodes for the application of supercapacitor; Journal of Power Sources; vol. 158; pp. 784-788; 2006.

Caruso et al.; Investigation of electrostatic interactions in polyelectrolyte multilayer fills: binding of anionic fluorescent probes to layers assemble onto colloids; Macromolecules; vol. 32; pp. 2317-2328 (1999).

Collins, Kim; Charge density-dependent strength of hydration and biological structure; Biophys. J.; vol. 72; pp. 65-76; Jan. 1997.

DeGennes; Scaling Concepts in Polymer Physics; Cornell U. Press; p. 223; 1979.

Jarvis et al.; Fuel cell / electrochemical capacitor hybrid for intermittent high power applications; J. Power Sources; vol. 79; pp. 60-63; 1999.

Jones et al.; The viscosity of aqueous solutions of strong electrolytes with special reference to barium chloride; J. Am. Chem. Soc.; vol. 51; pp. 2950-2964; 1929.

Losche et al., Detailed structure of molecularly thin polyelectrolyte multilayer films on solid substrates as revealed by neutron reflectometry; Macromolecules; 1998; vol. 31; pp. 8893-8906.

Salabat et al.; Thermodynamic and transport properties of aqueous trisodium citrate system at 298.15 K; J. Mol. Liq.; vol. 118; pp. 67-70; 2005.

(56) References Cited

OTHER PUBLICATIONS

Schlenoff et al., Mechanism of polyelectrolyte multilayer growth: charge overcompensation and distribution; Macromolecules; 2002, vol. 34, pp. 592-598.
Tuckerman et al.; High-performance heat sinking for VLSI; IEEE Electron Dev. Letts., vol. EDL-2, pp. 126-129; May 1981.
Tusek et al.; Surface characterisation of NH3 plasma treated polyamide 6 foils; Colloids and Surfaces A; vol. 195; pp. 81-95; 2001.
Kou et al.; Surface modification of microporous polypropylene membranes by plasma-induced graft polyerization of ?-allyl glucoside; Langmuir; vol. 19; pp. 6869-6875; 2003.
Yezek; Bulk conductivity of soft surface layers: experimental measurement and electrokinetic implications; Langmuir; 2005; vol. 21; pp. 10054-10060.
Krasemann et al.; Self-assembled polyelectrolyte multilayer membranes with highly improved pervaporation separation of ethanol/water mixtures; J of Membrane Science; vol. 181; No. 2; pp. 221-228; 2001.
Adamcyk et al., Characterization of Polyelectrolyte Multilayers by the Streaming Potential Method, Langmuir, 2004, vol. 20, 10517-10525.
Bello et al; Electroosmosis of polymer solutions in fused silica capillaries; Electrophoresis; vol. 15; pp. 623-626; 1994.
Boger, D.; Demonstration of upper and lower Newtonian fluid behaviour in a pseudoplastic fluid; Nature; vol. 265; pp. 126-128 (1977).
Buchholz et al.; Microchannel DNA sequencing matrices with switchable viscosities; Electrophoresis; vol. 23; pp. 1398-1409; 2002.
Chaiyasut et al.; Estimation of the dissociation constants for functional groups on modified and unmodified gel supports from the relationship between electroosmotic flow velocity and pH; Electrophoresis; vol. 22; pp. 1267-1272; 2001.
Decher, Fuzzy Nanoassemblies: Toward Layers Polymeric Multicomposites, Science, 1997, vol. 277, pp. 1232-1237.
Greene, George et al., Deposition and Wetting Characteristics of Polyelectrolyte Multilayers on Plasma-Modified Porous Polyethylene, Langmuir, 2004, vol. 20, pp. 2739-2745.
Gurau et al.; On the mechanism of the hofmeister effect; J. Am. Chem. Soc.; 2005; vol. 126; pp. 10522-10523.
Hunter; Foundations of Colloid Science vol. II (Oxford Univ. Press, Oxford) pp. 994-1002; (1989).
Jacobasch et al.; Adsorption of ions onto polymer surfaces and its influence on zeta potential and adhesion phenomena, Colloid Polym Sci.; vol. 276: pp. 434-442 (1998).
Jenkins, Donald et al., Viscosity B-Coefficients of Ions in Solution, Chem. Rev. 1995, vol. 95, pp. 2695-2724.
Jomaa et al., Salt-Induced Interdiffusion in Multilayers Films: A Neutron Reflectivity Study, Macromolecules; 2005; vol. 38, pp. 8473-8480.
Kiriy, Anton et al., Cascade of Coil-Globule Conformational Transitions of Single Flexible Polyelectrolyte Molecules in Poor Solvent, J. Am. Chem. Soc.; 2002; vol. 124, pp. 13454-13462.
Manz et al.; Electroosmotic pumping and electrophoretic separations for miniaturized chemical analysis systems; J. Micromach. Microeng.; vol. 4; pp. 257-265; 1994.
Mika et al., A new class of polyelectrolyte-filled microfiltration membranes with environmentally controlled porosity, Journal of Membrane Science; 1995, vol. 108, pp. 37-56.
Park, Juhyun et al., Polyelectrolyte Multilayer Formation on Neutral Hydrophobic Surfaces, Macromolecules; 2005, vol. 38, pp. 10542-10550.
Salomaeki et al., The Hofmeister Anion Effect and the Growth of Polyelectrolyte Multilayers, Langmuir; 2004, vol. 20, pp. 3679-3683.
Sankaranarayanan et al.; Chap. 1: Anatomical and pathological basis of visual inspection with acetic acid (VIA) and with Lugol's iodine (VILI); A Practical Manual on Visual Screening for Cervical Neoplasia; IARC Press; 2003.

Schoenhoff, J.; Layered polyelectrolyte complexes: physics of formation and molecular properties, Journal of Physics Condensed Matter; 2003, vol. 15, pp. R1781-R1808.
Schweiss et al., Dissociation of Surface Functional Groups and Preferential Adsorption of Ions on Self-Assembled Monolayers Assessed by Streaming Potential and Streaming Current Measurements, Langmuir; 2001, vol. 17, pp. 4304-4311.
Takamura, Y., et al., "Low-Voltage Electroosmosis Pump and Its Application to On-Chip Linear Stepping Pneumatic Pressure Source," Abstract, Micro Total Analysis Systems, 2001, pp. 230-232.
Weidenhammer, Petra et al., Investigation of Adhesion Properties of Polymer Materials by Atomic Force Microscopy and Zeta Potential Measurements, Journal of Colloid and Interface Science, vol. 180, pp. 232-236 (1996).
Wong et al., Swelling Behavior of Polyelectrolyte Multilayers in Saturated Water Vapor, Macromolecules; 2004, vol. 37, pp. 7285-7289.
Ye et al.; Capillary electrochromatography with a silica col. with dynamically modified cationic surfactant; Journal of Chromatography A; vol. 855; pp. 137-145; 1999.
Yoo et al., Controlling Bilayer Composition and Surface Wettability of Sequentially Adsorbed Multilayers of Weak Polyelectrolytes, Macromolecules; 1998, vol. 31, pp. 4309-4318.
Zeng, S. et al., "Fabrication and characterization of electroosmotic micropumps," Sensors and Actuators, B 79: pp. 107-114 (2001).
Zhang et al.; Specific ion effects on the water solubility of macromolecules: Pnipam and the Hofmeister series; J. Am. Chem. Soc.; vol. 127; pp. 14505-14510; 2005.
US 6,406,905, 06/2002, Parce et al. (withdrawn).
Anex et al.; U.S. Appl. No. 12/728,844 entitled "Electrokinetic Pump Designs and Drug Delivery Systems," filed Mar. 22, 2010 .
Adamson et al., Physical Chemistry of Surfaces, pp. 185-187 (Wiley, NY 1997).
Ananthakrishnan et al., Laminar Dispersion in capillaries; A.I. Ch.E. Journal, 11(6):1063-1072 (Nov. 1965).
Aris, R.; On the dispersion of a solute in a fluid flowing through a tube. Proceedings of the Royal Society of London; Series A, Mathematical and Physical Sciences; vol. 235(1200); pp. 67-77; 1956.
Baquiran et al.; Lippincott's Cancer Chemotherapy Handbook; 2nd Ed; Lippincott; Philadelphia; 2001.
Becker et al; Polymer microfabrication methods for microfluidic analytical applications; Electrophoresis; vol. 21; pp. 12-26; 2000.
Belfer et al.; Surface Modification of Commercial Polyamide Reverse Osmosis Membranes; J. Membrane Sci.; 139; pp. 175-181; 1998.
Boerman et al.; Pretargeted radioimmunotherapy of cancer: progress step by step; J. Nucl. Med.; vol. 44; No. 3; pp. 400-411; Mar. 2003.
Braun et al.; Small-angle neutron scattering and cyclic voltammetry study on electrochemically oxidized and reduced pyrolytic carbon; Electrochimica Acta; vol. 49; pp. 1105-1112; 2004.
Burgreen et al.; Electrokinetic flow in ultrafine capillary slits; The Journal of Physical Chemistry, 68(95): pp. 1084-1091 (May 1964).
Chatwin et al.; The effect of aspect ratio on longitudinal diffusivity in rectangular channels; J. Fluid Mech.; vol. 120; pp. 347-358 (1982).
Chu et al.; Physicians Cancer Chemotherapy Drug Manual 2002; Jones and Bartlett Publisheer; Massachusetts; 2002.
Churchill et al.; Complex Variables and Applications; McGraw-Hill, Inc. New York; 1990.
Conway, B.E.; Electrochemical Supercapacitors Scientific Fundamentals and Technological Applications; Kluwer Academic/Plenum Publishers; pp. 12-13, pp. 104-105, and pp. 192-195; 1999.
Cooke Jr., Claude E.; Study of electrokinetic effects using sinusoidal pressure and voltage; The Journal of Chemical Physics; vol. 23; No. 12; pp. 2299-2300; Dec. 1955.
Dasgupta et al.; Electroosmosis: a reliable fluid propulsion system for flow injection analysis; Anal. Chem.; vol. 66; pp. 1792-1798; 1994.
Doshi et al.; Three dimensional laminar dispersion in open and closed rectangular conduits; Chemical Engineering Science, 33; pp. 795-804 (1978).
Drott et al.; Porous silicon as the carrier matrix in microstructured enzyme reactors yielding high enzyme activities; J. Micromech. Microeng; vol. 7; pp. 14-23 (1997).

(56) References Cited

OTHER PUBLICATIONS

Gan et al.; Mechanism of porous core electroosmotic pump flow injection system and its application to determination of chromium(VI) in waste-water; Talanta; vol. 51; pp. 667-675 (2000).
Gennaro, A.R.; Remington: The Science and Practice of Pharmacy (20th ed.); Lippincott Williams & Wilkins. Philadelphia; 2000.
Gleiter et al.; Nanocrystalline Materials: A Way to Solids with Tunable Electronic Structures and Properties?; Acta Mater; 49; pp. 737-745; 2001.
Gongora-Rubio et al.; The utilization of low temperature co-fired ceramics (LTCC-ML) technology for meso-scale EMS, a simple thermistor based flow sensor; Sensors and Actuators; vol. 73; pp. 215-221; 1999.
Goodman and Gilman's "The Pharmacological Basis of Therapeutics;" (10th Ed.); Hardman et al. (editors); 2001.
Gritsch et al.; Impedance Spectroscopy of Porin and Gramicidin Pores Reconstituted into Supported Lipid Bilayers on Indium-Tin-Oxide Electrodes; Langmuir; 14; pp. 3118-3125; 1998.
Haisma; Direct Bonding in Patent Literature; Philips. J. Res.; vol. 49, pp. 165-170; 1995.
Jackson, J. D.; Classical Electrodynamics 2nd Ed. John Wiley & Sons, Inc. New York. 1962.
Jessensky et al.; Self-organized formation of hexagonal pore structures in anodic alumina; J. Electrochem. Soc.; vol. 145; (11); pp. 3735-3740 (Nov. 1998).
Jimbo et al.; Surface Characterization of Poly(acrylonitrite) Membranes: Graft-Polymerized with Ionic Monomers as Revealed by Zeta Potential Measurements; Macromolecules; vol. 31; pp. 1277-1284; 1998.
Johnson et al.; Dependence of the conductivity of a porous medium on electrolyte conductivity; Physical Review Letters; 37(7); pp. 3502-3510 (Mar. 1, 1988).
Johnson et al.; New pore-size parameter characterizing transport in porous media; Physical Review Letter; 57(20); pp. 2564-2567 (Nov. 17, 1986).
Johnson et al.; Theory of dynamic permeability and tortuosity in fluid-saturated porous media; J. Fluid Mech; 176; pp. 379-402 (1987).
Klein, F.; Affinity Membranes: a 10 Year Review; J. Membrance Sci.; vol. 179; pp. 1-27; 2000.
Kobatake et al.; Flows through charged membranes. I. flip-flop current vs voltage relation; J. Chem. Phys.; 40(8); pp. 2212-2218 (Apr. 1964).
Kobatake et al.; Flows through charged membranes. II. Oscillation phenomena; J. Chem. Phys.; 40(8); pp. 2219-2222 ( Apr. 1964).
Kotz et al.; Principles and applications of electrochemical capacitors; Electrochimica Acta; 45; pp. 2483-2498; 2000.
Liu et al.; Electroosmotically pumped capillary flow-injection analysis; Analytica Chimica Acta; vol. 283; pp. 739-745; 1993.
Liu et al.; Flow-injection analysis in the capillary format using electroosmotic pumping; Analytica Chimica Acta; vol. 268; pp. 1-6; 1992.
Ma et al.; A review of zeolite-like porous materials; Microporous and Mesoporous Materials; 37; pp. 243-252 (2000).
Martin et al.; Laminated Plastic Microfluidic Components for Biological and Chemical Systems; J. Vac. Sci. Technol.; vol. A 17; pp. 2264-2269; 1999.
Morrison et al.; Electrokinetic energy conversion in ultrafine capillaries; J. Chem. Phys.; 43; pp. 2111-2115 (1965).
Mroz et al.; Disposable Reference Electrode; Analyst; vol. 123; pp. 1373-1376; 1998.
Nakanishi et al.; Phase separation in silica sol-gel system containing polyacrylic acid; Journal of Crystalline Solids; 139; pp. 1-13 (1992).
Paul et al., Electrokinetic pump application in micro-total analysis systems mechanical actuation to HPLC; Micro Total Analysis Systems, pp. 583-590 (2000).
Paul et al.; Electrokinetic generation of high pressures using porous microstructures; Micro Total Analysis Systems, pp. 49-52 (1998).
Peters et al.; Molded rigid polymer monoliths as separation media for capillary electrochromatography; Anal. Chem.; 69; pp. 3646-3649 (1997).
Philipse, A.P., Solid opaline packings of colloidal silica spheres; Journal of Materials Science Letters; 8; pp. 1371-1373 (1989).
Pretorius et al.; Electro-osmosis: a new concept for high-speed liquid chromatography; Journal of Chromatography; vol. 99; pp. 23-30; 1974.
Rastogi, R.P.; Irreversible thermodynamics of electro-osmotic effects; J. Scient. Ind. Res.; (28); pp. 284-292 (Aug. 1969).
Rice et al.; Electrokinetic flow in a narrow cylindrical capillary; J. Phys. Chem.; 69(11); pp. 4017-4024 (Nov. 1965).
Roberts et al.; UV Laser Machined Polymer Substrates for the Development of Microdiagnostic Systems; Anal. Chem.; vol. 69; pp. 2035-2042; 1997.
Rosen, M.J.; Ch.2—Adsorption of surface-active agents at interfaces: the electrical double layer; Surfactants and Interfacial Phenomena, Second Ed., John Wiley & Sons, pp. 32-107.
Schmid et al.; Electrochemistry of capillary systems with narrow pores V. streaming potential: donnan hindrance of electrolyte transport; J. Membrane Sci.; 150; pp. 197-209 (1998).
Schmid, G.; Electrochemistry of capillary systems with narrow pores. II. Electroosmosis; J. Membrane Sci.; 150; pp. 159-170 (1998).
Skeel, Ronald T. (editor); Handbook of Chemotherapy (6th Ed.); Lippincott Williams & Wilkins; 2003.
Stokes, V. K.; Joining Methods for Plastics and Plastic Composites: An Overview; Poly. Eng. And Sci.; vol. 29; pp. 1310-1324; 1989.
Takata et al.; Modification of Transport Properties of Ion Exchange Membranes; J. Membrance. Sci.; vol. 179; pp. 101-107; 2000.
Taylor, G.; Dispersion of soluble matter in solvent flowing slowly through a tube; Prox. Roy. Soc. (London); 21; pp. 186-203; Mar. 31, 1953.
Uhlig et al.; The electro-osmotic actuation of implantable insulin micropumps; Journal of Biomedical Materials Research; vol. 17; pp. 931-943; 1983.
Van Brunt, Jennifer; Armed antibodies; Signals (online magazine); 11 pgs.; Mar. 5, 2004.
Vinson, J.; Adhesive Bonding of Polymer Composites; Polymer Engineering and Science; vol. 29; No. 19; pp. 1325-1331; Oct. 1989.
Watson et al.; Recent Developments in Hot Plate Welding of Thermoplastics; Poly. Eng. and Sci.; vol. 29; pp. 1382-1386; 1989.
Weston et al.; Instrumentation for high-performance liquid chromatography; HPLC and CE, Principles and Practice, (Chp. 3) pp. 82-85, Academic Press.
Wijnhoven et al.; Preparation of photonic crystals made of air spheres in titania; Science; 281; pp. 802-804 (Aug. 7, 1998).
Yazawa, T., Present status and future potential of preparation of porous glass and its application; Key Engineering Materials; 115; pp. 125-146 (1996).

* cited by examiner

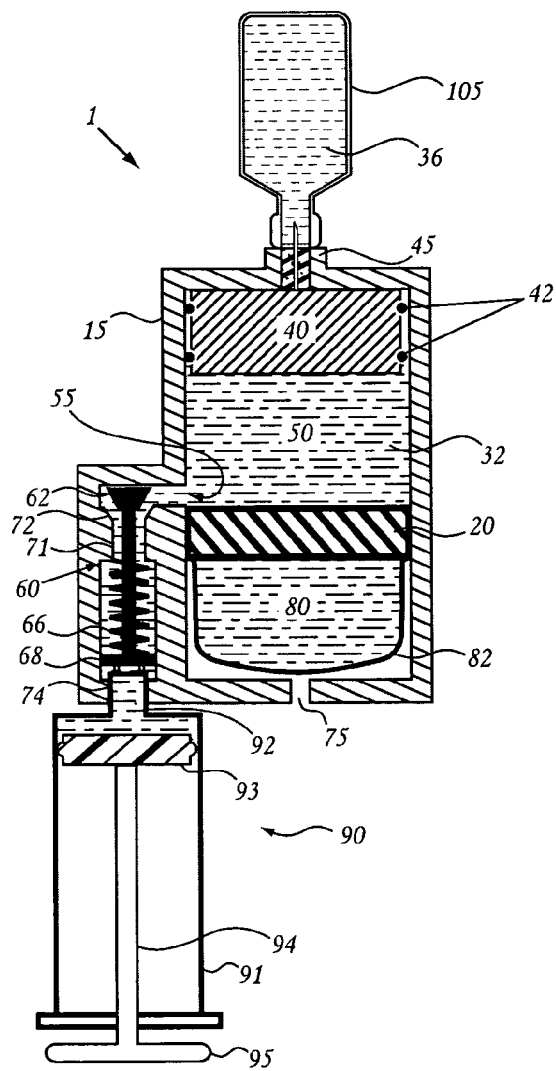
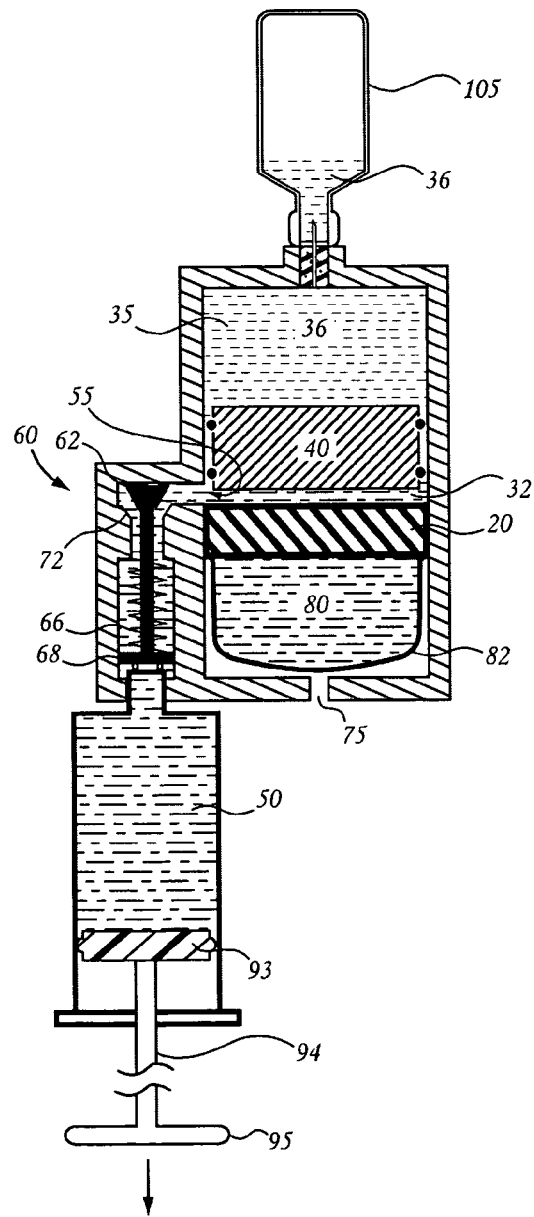
FIG. 2A
FIG. 2B

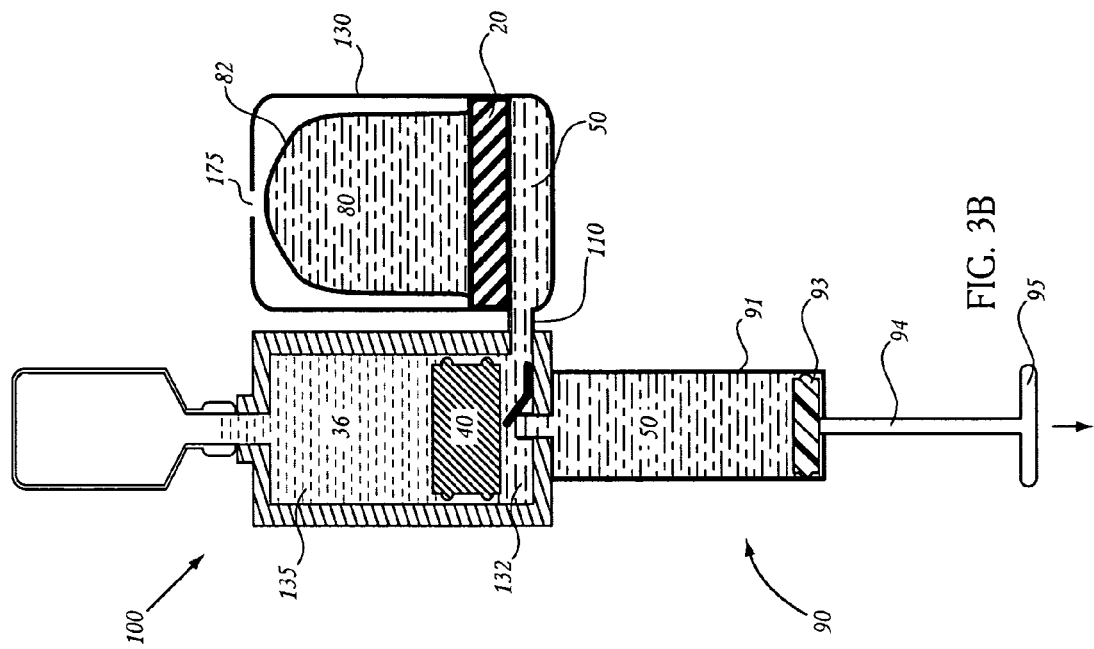
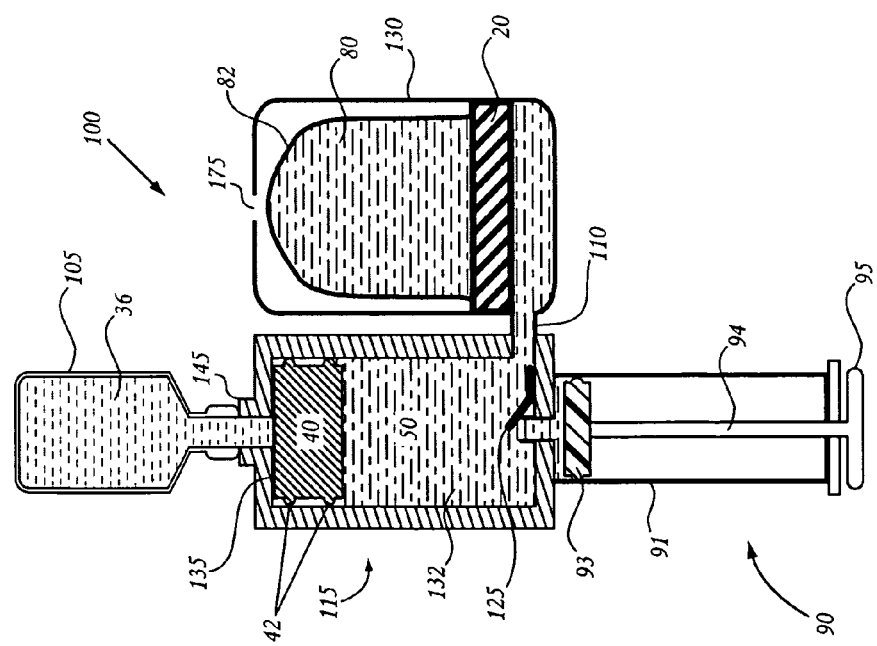
FIG. 3A
FIG. 3B

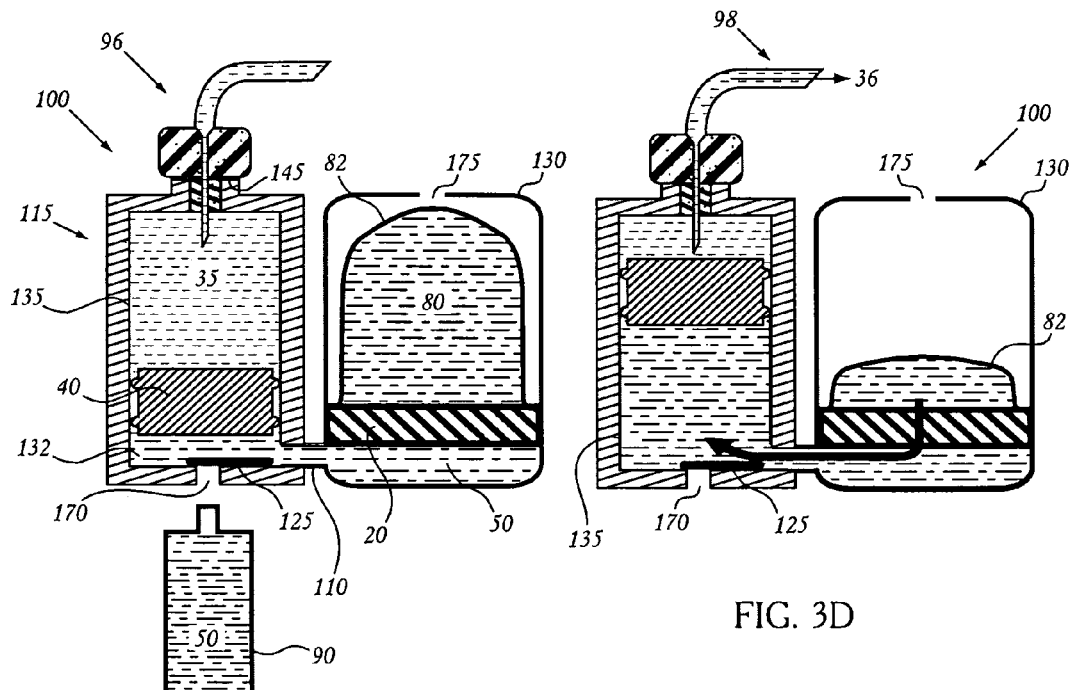
FIG. 3C
FIG. 3D
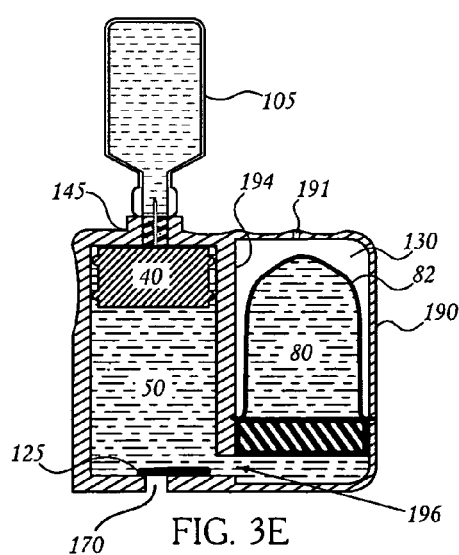
FIG. 3E
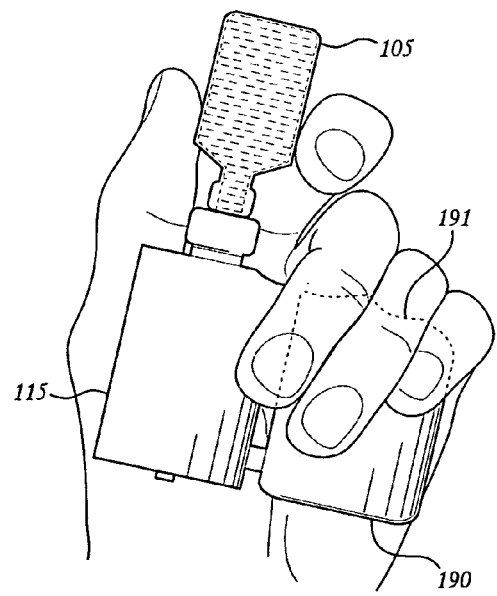
FIG. 3F

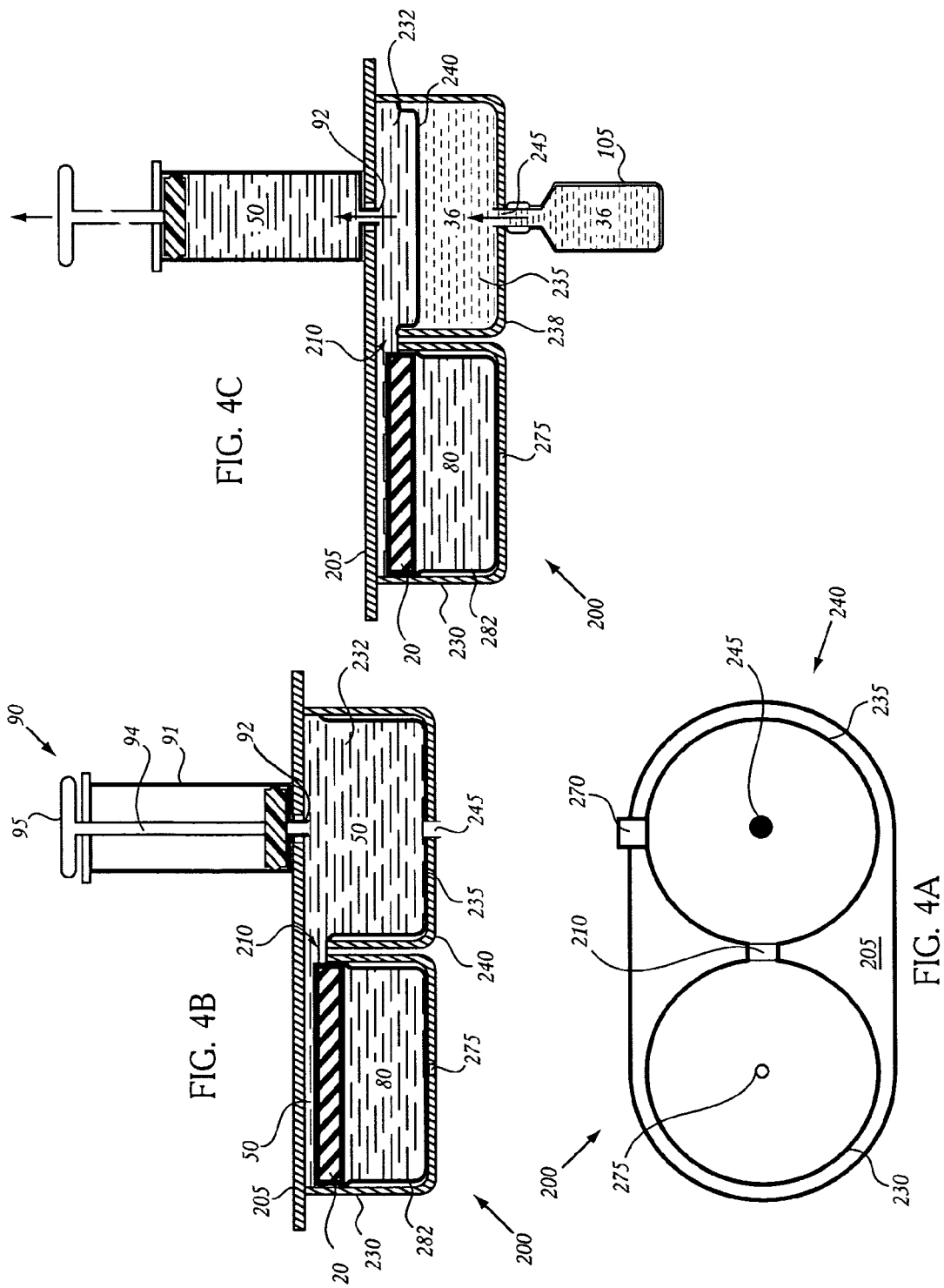

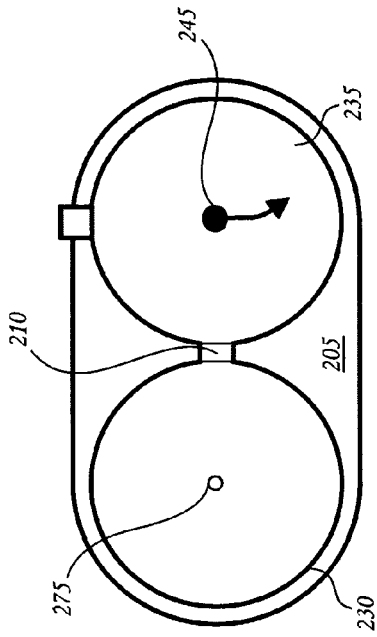
FIG. 4F
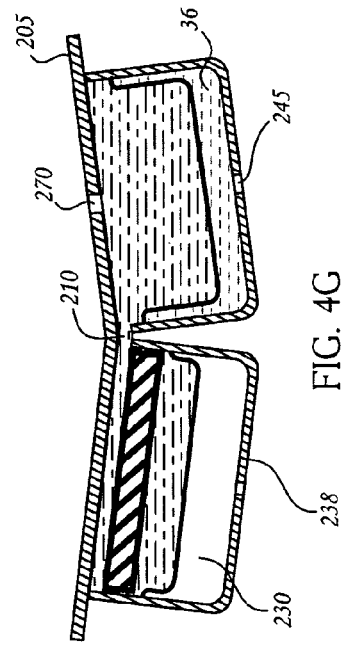
FIG. 4G
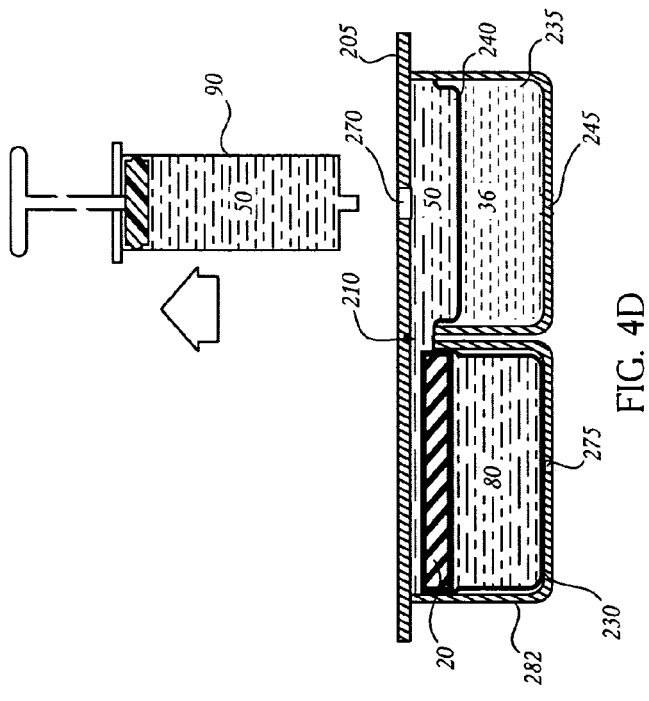
FIG. 4D
FIG. 4E

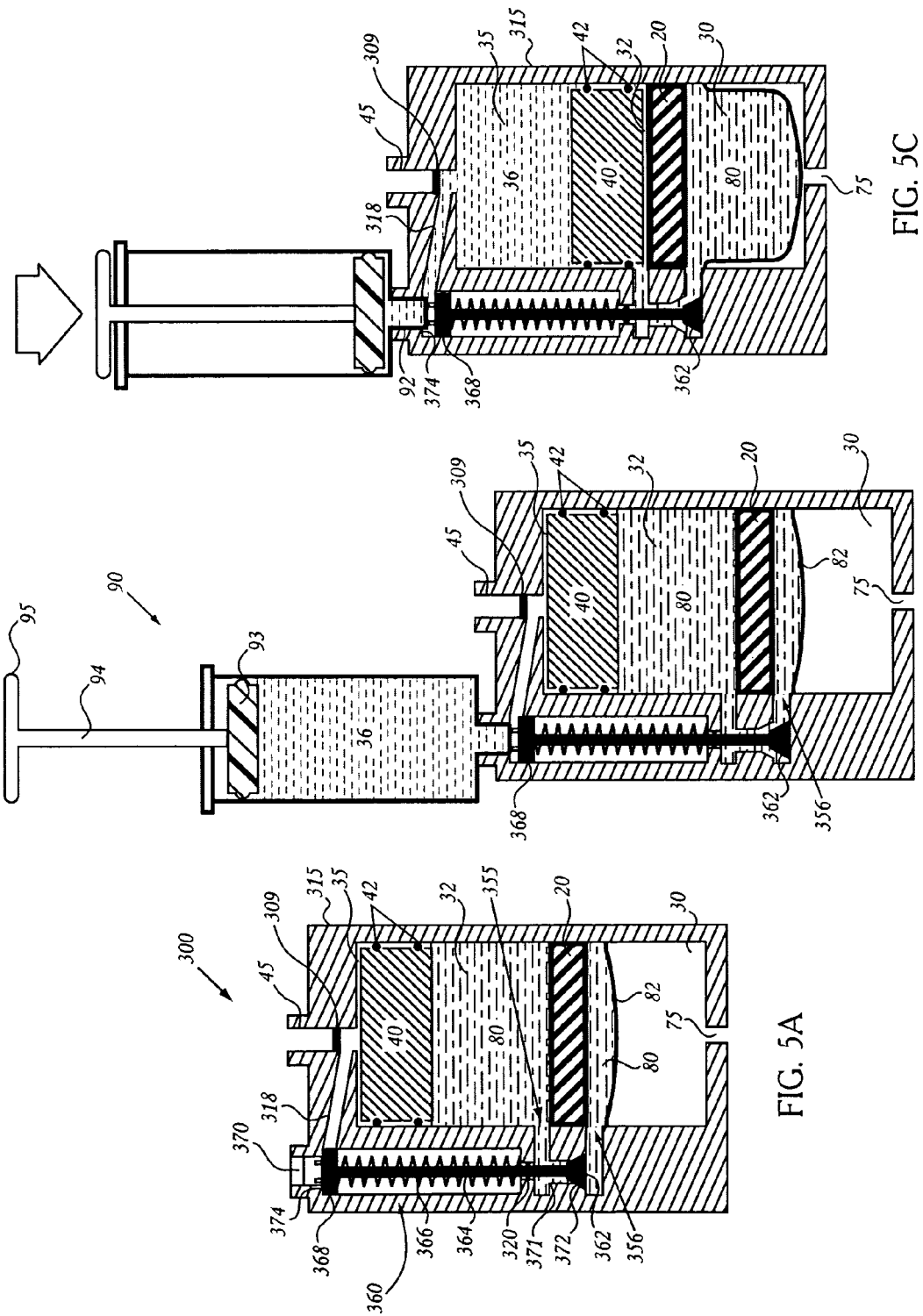

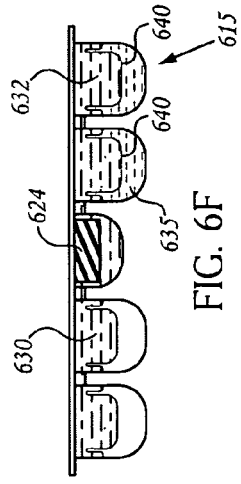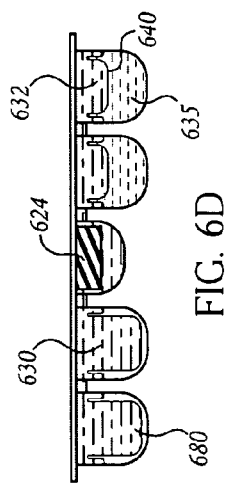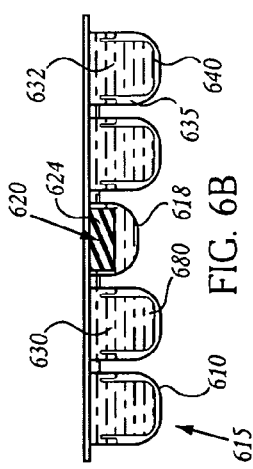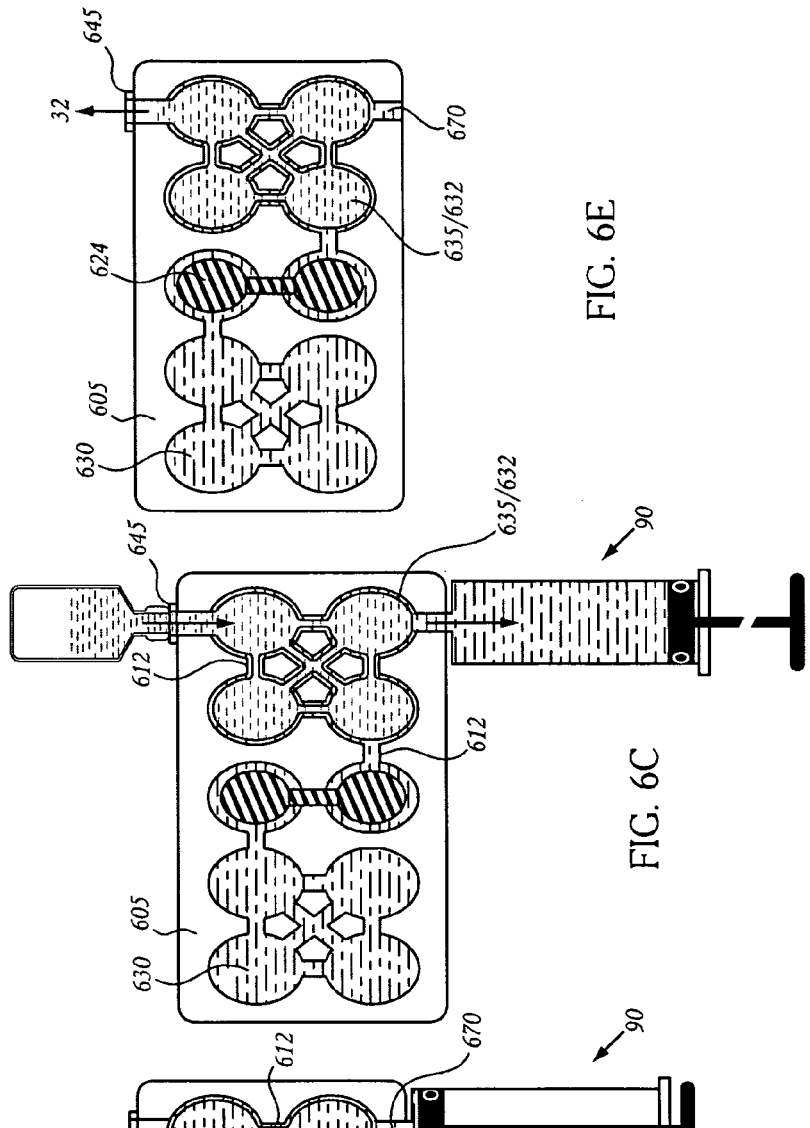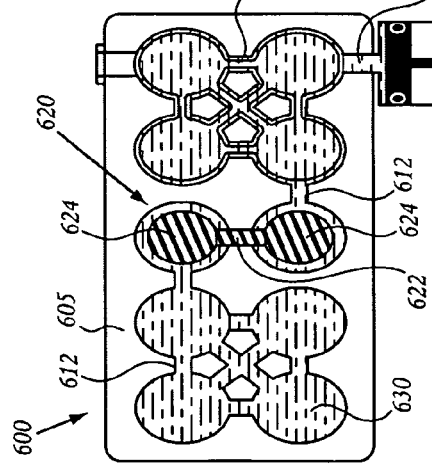

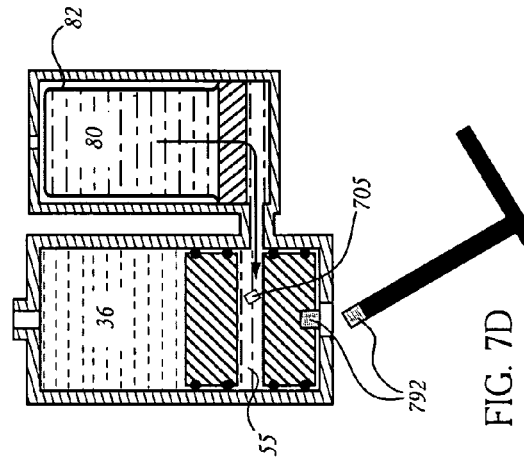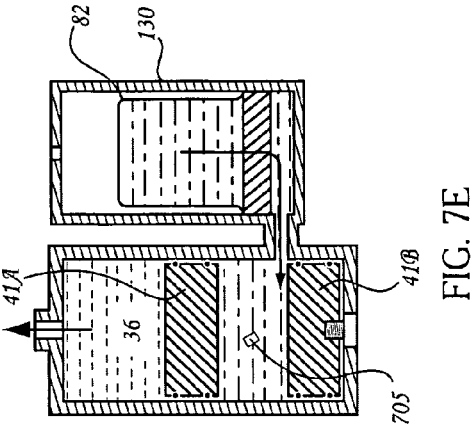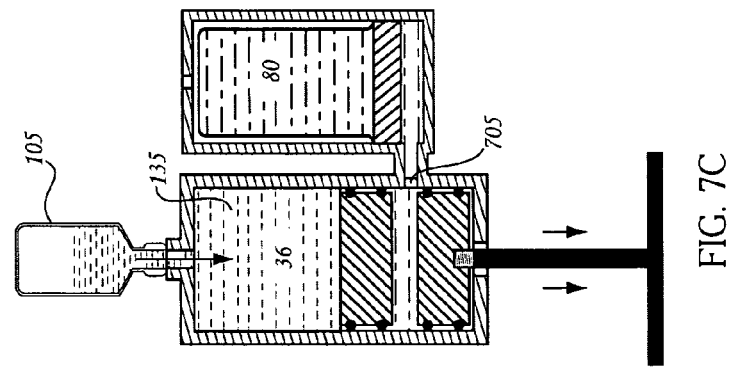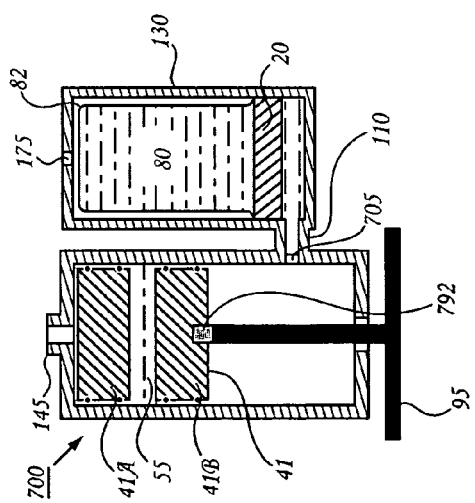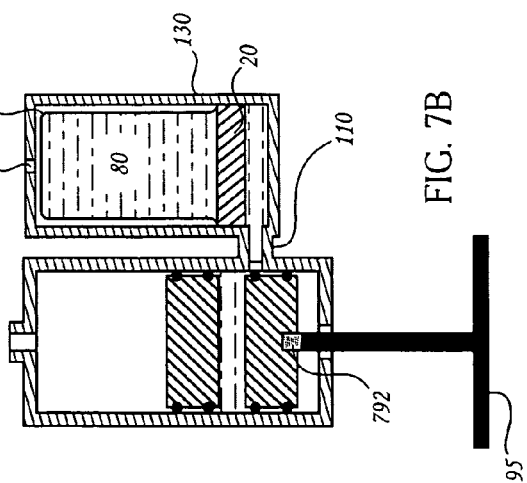

ELECTROKINETIC PUMP DESIGNS AND DRUG DELIVERY SYSTEMS

CROSS-REFERENCE TO RELATED APPLICATIONS

This application claims the benefit of U.S. Provisional Application No. 60/739,390, filed Nov. 23, 2005, titled "Electrokinetic Pump Designs and Drug Delivery Systems" which is incorporated herein by reference in its entirety. This application is related to the following patent applications: U.S. application Ser. No. 11/603,926, filed Nov. 22, 2006, titled "Electrokinetic Pump Designs and Drug Delivery Systems: Publication No. US-2007-0224055-A1, now abandoned; U.S. application Ser. No. 10/198,223, filed Jul. 17, 2002, titled "Laminated Flow Devices: now U.S. Pat. No. 7,364,647; U.S. application Ser. No. 10/273,723, filed Oct. 18, 2002, titled "Electrokinetic Device Having Capacitive Electrodes: now U.S. Pat. No. 7,235,164; U.S. application Ser. No. 10/322,083, filed Dec. 17, 2002, titled "Electrokinetic Device Having Capacitive Electrodes: now U.S. Pat. No. 7,267,753; and U.S. application Ser. No. 11/112,867, filed Apr. 21, 2005, titled "Electrokinetic Delivery Systems, Devices and Methods," now U.S. Pat. No. 7,517,440, each of which are incorporated herein by reference in its entirety.

BACKGROUND OF THE INVENTION

Pumps and pumping systems exist for the delivery of various fluids. A variety of pumps are used in a number of various different configurations and uses. Pumps are used for infusion of drugs or delivery of drugs into mammals, the sterility of the drugs is very important. In addition, contamination of the drug or delivery fluid from the pump system should be reduced or eliminated. Additionally, it remains an important aspect to minimize contact between the drug to be delivered and the internal components of the pump being used to deliver the drug. Filling or preparing the drug or fluid for delivery should not be time consuming. These and other difficulties are encountered using conventional filling and pumping systems.

Related U.S. application Ser. No. 11/112,867 filed Apr. 21, 2005 titled, "Electrokinetic Delivery Systems, Devices and Methods," discloses a technique for filling a pump with fluid for delivery. This technique involves operating the pump system in reverse to draw the delivery fluid into the pump. Then, after filling the pump with the delivery fluid, the pump direction is reversed and the delivery fluid is delivered from the pump. Reversing pump direction may be a good solution for small amounts of fluid or for pump configurations that have a very high linear flow rate. However, the time requirements for loading large volumes of delivery fluid using this technique may be prohibitive for time conscious applications and problematic for later pump operation.

What are needed are improved techniques for providing the delivery fluid into the pumping system. The pump filling procedures should be simple and require small amounts of time.

SUMMARY OF THE INVENTION

One embodiment of the invention provides a fluid delivery system having a first chamber, a second chamber and a third chamber; a flow-through pump element separating the first chamber from the second chamber; a moveable pump element separating the second chamber from the third chamber; a first outlet in communication with the third chamber; and a second outlet in communication with the second chamber. In one aspect, the second chamber and the third chamber are within a single housing. In another aspect, the second outlet is in communication with the first chamber. In yet another aspect, the second outlet is in communication with the exterior of the housing. In yet another aspect, there is a moveable pump element in the first chamber. In one aspect, the moveable pump element is separated by the operation of the flow-through pump element. In one aspect, the moveable pump element is a diaphragm. In another aspect, the flow-through pump element is an electrokinetic pump. In another aspect, the electrokinetic pump has electrodes having a double layer capacitance of greater than $10^{-4}$ microfarad/cm$^2$. In another aspect, there is a valve separating the second outlet from the exterior of the housing. In another aspect, there is a flap separating the second outlet from the exterior of the housing. In another alternative aspect, there is provided a valve positioned in the housing that when actuated allows communication between the third chamber and the exterior of the housing and communication between the second chamber and the first chamber. In another embodiment, a seal separates the second chamber from the moveable element. In yet another aspect there is provided a vent in communication with the first chamber, the second chamber or the third chamber. In yet another embodiment, there is a portion of the housing is shaped to conform to an anatomical contour. In still another alternative, the second chamber or the third chamber comprises a plurality of cells. In one aspect, the plurality of cells are interconnected.

In another embodiment, there is provided a method of operating a fluid delivery system having a first chamber, a second chamber and a delivery chamber by reducing the volume of the second chamber while increasing the volume of the delivery chamber without operation of a flow-through pump element that separates the second chamber from the first chamber. In one aspect, the reducing step is performed by moving a moveable pump element that separates the second chamber from the delivery chamber. In another aspect, fluid is moved within the second chamber from the second chamber to, a location outside of the housing. In yet another aspect, fluid moves within the second chamber from the second chamber to a location inside of the housing. In one aspect, the fluid moves to a location inside of the first chamber. In another aspect, the method includes opening a fluid pathway from outside the housing to the second chamber before the reducing step. In another aspect, opening a fluid pathway comprises opening a valve. In another aspect, the method includes operating a flow-through pump element that separates the first chamber from the second chamber to reduce the volume of the first chamber and the third chamber. In yet another aspect, the method includes operating a flow-through pump element that separates the first chamber from the second chamber to reduce the volume of the first chamber and increase the volume of the second chamber. In another aspect, the method includes operating a flow-through pump element that separates the first chamber from the second chamber to move a moveable pump element that separates the second chamber from the delivery chamber. In yet another aspect, the method includes operating a flow-through pump element that separates the first chamber from the second chamber to move a delivery fluid within the delivery chamber to a location outside of the housing. In yet another aspect, the method includes operating a valve within the housing to allow fluid flow from outside the housing into the delivery chamber. In another aspect, operating the valve allows fluid flow from the second chamber to the first chamber. In another aspect, the method includes the step of operating a flow-through pump element that separates the first chamber from the second chamber to rupture a seal in the second chamber. In yet another aspect, the method includes the step of operating a flow-through pump element that separates the first chamber from the second chamber to separate a moveable pump element positioned between the second chamber and the delivery chamber.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2D illustrate the filling an operation of another fluid delivery system embodiment;

FIGS. 3A-3F illustrate the filling and operation of another fluid delivery system embodiment;

FIGS. 4A-4G illustrate the filling and operation of another alternative fluid delivery system embodiment;

FIGS. 5A-5F illustrate the filling and operation of yet another alternative fluid delivery system embodiment;

FIGS. 6A-6F illustrate the filling and operation of an alternative fluid delivery system having a plurality of cells used for chambers;

FIGS. 7A-7E illustrate the filling and operation of an alternative fluid delivery system having a split moveable pump element.

DETAILED DESCRIPTION OF THE INVENTION

Figures 1A, 1B:
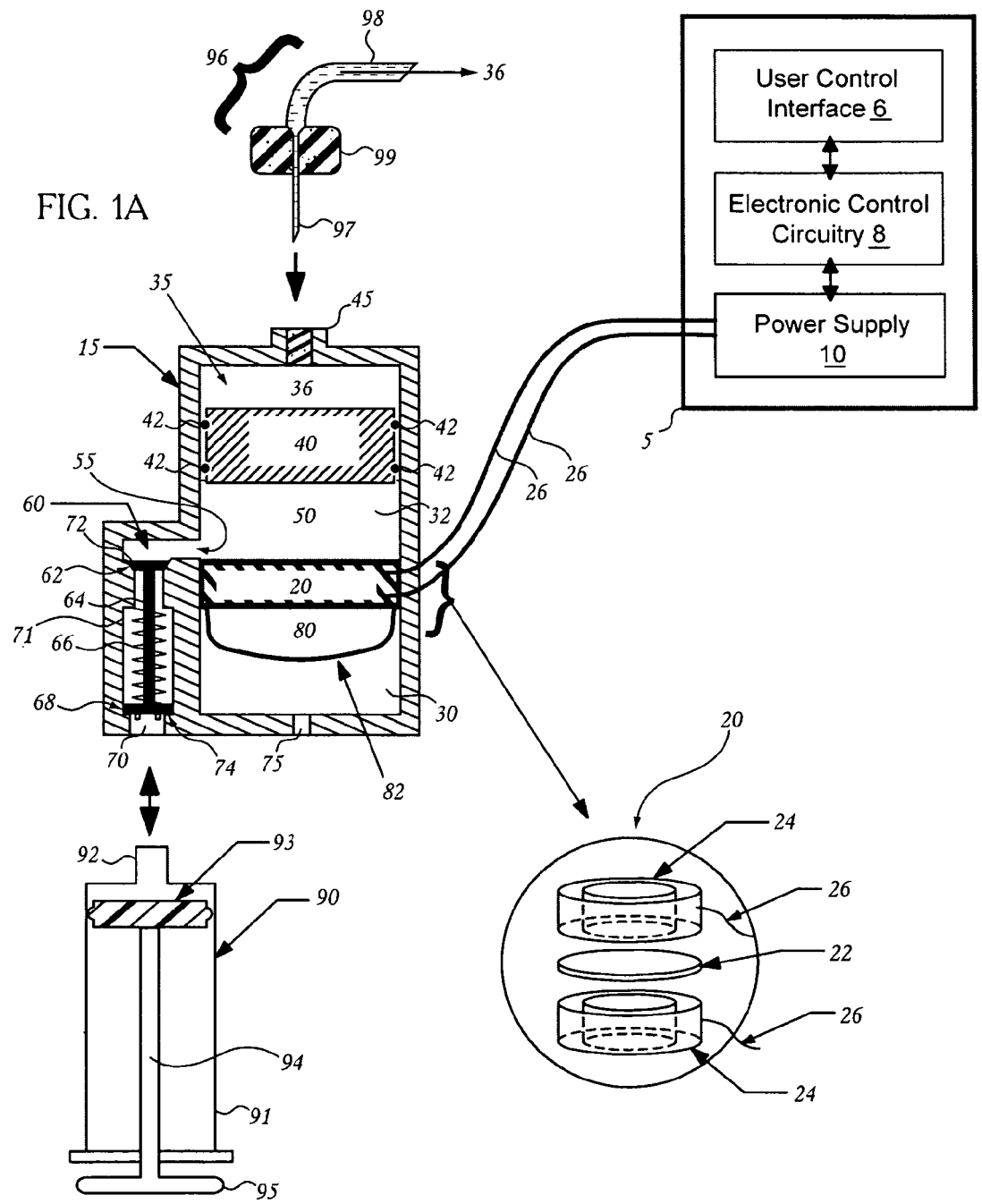
FIG. 1A is a fluid delivery system.
FIG. 1B is an enlarged view of the components of an exemplary electrokinetic pump.

FIG. 1A illustrates a cross section view of one embodiment of a fluid delivery system 1. The fluid delivery system has a first chamber 30, a second chamber 32 and a third chamber 35. A flow-through pump element 20 (such as electrokinetic pump, as shown in FIG. 1B) separates the first chamber 30 from the second chamber 32. A moveable pump element 40 (such as a floating piston, as shown) separates the second chamber 32 from the third chamber 35. While in this illustrative embodiment the moveable element 40 is a floating piston, any device that provides a moveable barrier may be used as will be illustrated in the examples that follow. In this embodiment, the first, the second and the third chambers are within a single housing 15. Seals 42 are used to seal the moveable pump element 40 as it moves within the housing 15. An outlet 45 provides communication between the third chamber 35 and the exterior of housing 15. An outlet 55 provides communication between the second chamber 32 and the exterior of housing 15. In this embodiment, a valve 60 separates the second outlet 55 from the exterior of housing 15. Suitable materials for construction of components include polypropylene, polycarbonate and medical grade plastics.

As illustrated, a conduit 71 connects the outlet 55 to the opening 70. A valve 60 in the conduit 71 controls fluid flow from the outlet 55 to the opening 70. The valve 60 has a disc 62, stem 64, a spring 66 and a disc or seal 68. Seats 72, 74 in the housing are shaped to seal with, respectively, discs or seals 62, 68. Valve 60 is shown in the closed position where spring 66 holds discs 68, 62 in place against seats 72, 74. In this embodiment, conduit 71 and valve 60 are disposed in a wall of housing 15. Other configurations are possible such as a separate valve assembly that attaches directly to port 55 or a valve/conduit configuration that ports through the pump element 20 rather than around the pump element 20 as shown.

In the illustrated embodiment, the first chamber 30 contains a moveable pump element 82 (by way of non-limiting example, a diaphragm adjacent the pump element 20). The first chamber 30 also contains a vent 75, if needed to ensure free movement of the moveable element 82. The space between the diaphragm 82 and the pump element 20 contains a buffer or pump fluid 80 that is selected to operate with the type of pump element used. If the pump element 20 is an electrokinetic pump, then the buffer 80 would be an electrolyte selected to operate with the electrode and membrane materials and desired operation of the pump. Examples of specific electrolytes and other details of electrokinetic pumps are described in co-pending and commonly assigned patent application serial numbers U.S. application Ser. No. 10/198,223, filed Jul. 17, 2002 titled, "Laminated Flow Devices"; U.S. application Ser. No. 10/273,723 filed Oct. 18, 2002 titled, "Electrokinetic Device Having Capacitive Electrodes"; U.S. application Ser. No. 10/322,083 filed Dec. 17, 2002 titled, "Electrokinetic Device Having Capacitive Electrodes" and U.S. application Ser. No. 11/112,867 filed Apr. 21, 2005 titled, "Electrokinetic Delivery Systems, Devices and Methods," each of which are incorporated herein by reference in its entirety.

The pump element 20 is connected to supporting electronics 5 by electrical connectors 26. The supporting electronics 5 may be altered depending upon the type of pump element(s) used but will generally include a user control interface 6, electronic control circuitry 8 and a power supply 10. The user control interface 6 may be a touch screen or other input means to allow a user to operate the delivery system, select a program or otherwise provide programming instructions to the system. The electronic control circuitry contains the programming instructions needed to translate the user inputs into commands to operate the pump element. The electronic control circuitry also regulates the power supply to achieve user desired pumping characteristics such as flow rate and delivery timing. The power supply 10 may contain a battery or the delivery system may be plugged into an electrical supply. The supporting electronics are conventional and will be understood by those of ordinary skill in the art.

An exploded view of one type of pump element 20 is shown in FIG. 1B. The pump element 20 shown in FIG. 1B is an electrokinetic pump element. Electrokinetic pump element contains a porous membrane material 22 between two capacitive electrodes 24. Illustrative electrode materials include carbon aero gel or carbon nanofoam. One example of a suitable porous membrane is a microporous filter having a pore size ranging from tens of nanometers to micron size. In one embodiment, the preferred pore size is 100-200 nanometers.

The capacitive electrodes are connected to the supporting electronics 5 by electrical connectors 26. The pump element contains a pump fluid or buffer 80 that is moved through the membrane 22 from one electrode towards the other electrode depending on how a voltage is applied between the electrodes 24. The electrokinetic flow produced by the pump element 20 may be in one direction (from one electrode to the other electrode) or may alternate directions of flow (towards one electrode and then away from that electrode and towards the other electrode). Examples of electrokinetic pumps configurations, electrolytes, electrodes, membranes (also referred to as porous dielectric materials) and other details of are described in co-pending and commonly assigned patent applications: U.S. application Ser. No. 10/198,223, filed Jul. 17, 2002 titled, "Laminated Flow Devices"; U.S. application Ser. No. 10/273,723 filed Oct. 18, 2002 titled, "Electrokinetic Device Having Capacitive Electrodes"; U.S. application Ser. No. 10/322,083 filed Dec. 17, 2002 titled, "Electrokinetic Device Having Capacitive Electrodes" and U.S. application Ser. No. 11/112,867 filed Apr. 21, 2005 titled, "Electrokinetic Delivery Systems, Devices and Methods," each of which are incorporated herein by reference in its entirety.

Optionally, a storage fluid 50 fills the second chamber. The storage fluid 50 may be a fluid used to maintain the integrity of the pump element 20 during storage or prior to operation. The storage fluid 50 may be the same or different than the fluid 80 stored in the first chamber. The storage fluid 50 may also be a pump fluid (by way of non-limiting example, such as electrolyte suited to operation in an electrokinetic pump) moved by operation of the pump element 20. A delivery fluid 36 is contained in the third chamber 35. In some embodiments, the delivery fluid is a drug, a pharmacological or therapeutic agent, or other substance to be delivered by operation of the pump element 20. FIG. 1A also illustrates a conventional syringe 90 having a body 91 with a tip 92. A plunger 93 is attached to handle 95 by shaft 94 is disposed within the body 91.

A method for operating a fluid delivery system having a first chamber, a second chamber and third or delivery-chamber may be appreciated through reference to FIGS. 2A-2D. FIGS. 2A-2D illustrate a fluid delivery system 1 similar to that shown in FIGS. 1A and 1B and similar reference numbers will be used for the same components. This configuration is referred to as a vertical or in-line chamber. This chamber is so designated since the components in housing 15 are arranged coaxially within one cylindrical housing 15. As such, the first chamber 30, the second chamber 32, the pump element 20 and the third chamber 35 are axially aligned within housing 15. The exception is the bypass valve 60 and associated conduit 71 and opening 70 that are located off to one side. It is to be appreciated that in-line valve/conduit/opening configurations are possible such as where the valve/conduit/opening are adapted to pass through the pump element 20 and first chamber 30, for example.

FIG. 2A illustrates the beginning of a filling process to load the third chamber 35 (the delivery chamber) with a delivery fluid 36. As shown in the illustrated embodiment, a vial 105 filled with a delivery fluid 36 is attached to the outlet 45. One way to accomplish filling is to operate the flow-through pump element in reverse to reduce the volume in chamber two and increase the volume of chamber 3 by moving the moveable pump element 40 downward. Running the pump element 30 in reverse may be slow and inefficient, however.

A more efficient filling operation is accomplished by reducing the volume of the second chamber while increasing the volume of the delivery chamber without operation of the flow-through pump element 20 that separates the second chamber from the first chamber. This operation is illustrated in FIGS. 2A and 2B. First, open a fluid pathway from outside the housing 15 to the second chamber before performing the volume reducing step. In the illustrated embodiment of FIGS. 2A and 2B, the fluid pathway is provided by opening valve 60. Valve 60 is opened by inserting the syringe tip 92 into opening 70 to compress spring 66 and raise discs 68, 62 off of seats 74, 72, respectively. Storage fluid 50 may be removed from the second chamber along the pathway through outlet 55 and conduit 71 to outside the housing 15. Withdrawing syringe handle 95 and plunger 93 draws storage fluid 50 from the second chamber 35 causing the moveable pump element 40 to reduce the volume of the second chamber while increasing the volume of the delivery or third chamber as shown in FIG. 2B. This same action by the moveable element 40 draws delivery fluid 36 from the vial into the increasing volume of the third chamber 35.

The bypass valve 60 enables the syringe port or opening 70 to be at the bottom of the housing 15. Locating the opening 70 at the bottom of housing 15 allows effective purging of air during the filling process. Alternatively, the syringe 90 could be attached to draw horizontally through a conduit and a valve aligned with outlet 55. The compact size of the illustrated configuration achieves a small diameter design due to all principle components (by way of non-limiting example, the three chambers, moveable pump element or floating piston 40, diaphragm 82, and pump element 20) being positioned along a single axis. While the valve 60 and associated conduit 71 are not on the same axis, the valve and conduit can be made small, thereby resulting in a minimal increase of the outer diameter of the housing 15. In these illustrative embodiments, the valve 60 and conduit 71 are enlarged to show detail and are not illustrated to scale. Other types of valves, seals or a septum that can be opened when a syringe is attached may also be used.

When the syringe tip 92 opens valve 60 and the syringe piston handle 95 is pulled back, the delivery liquid 36 is aspirated into the third chamber or the delivery chamber 35. FIG. 2A illustrates a fluid delivery system 1 that is pre-filled with storage fluid 50, buffer 80 and purged of air. Syringe tip 92 is shown inserted into outlet 70 to lift discs 68, 62 to place valve 60 in the open position. A vial 105 or other suitable container containing the delivery fluid 36 is attached to the outlet 45 in such a way that the contents of the vial 105 are in communication with the delivery chamber 35. Filling without the introduction of air is facilitated since moveable element 40 is in the top position at the beginning of the filling operation as shown in FIG. 2A. However, air may be introduced as part of a conventional drug aspiration technique.

FIG. 2B illustrates removing a fluid from the second chamber 32 and using the removal of the fluid to introduce a delivery fluid without passing the delivery fluid through a pump element inside the housing 15. In this illustrative example, the fluid movement is accomplished by withdrawing the syringe handle 95 to draw the storage fluid 50 from the second chamber 32 via port 55, conduit 71 and the open valve 60 into the syringe body 91. Withdrawal of the storage fluid 50 also draws down the moveable element 40 (by way of non-limiting example, a floating piston in this embodiment). The moveable element 40 in turn draws the delivery fluid 36 from the vial 105 through outlet 45 and into the delivery chamber 35. The delivery fluid 36 is drawn into the increasing volume of the delivery chamber 35 between the outlet 45 and the moveable element 40.

Figures 2C, 2D:
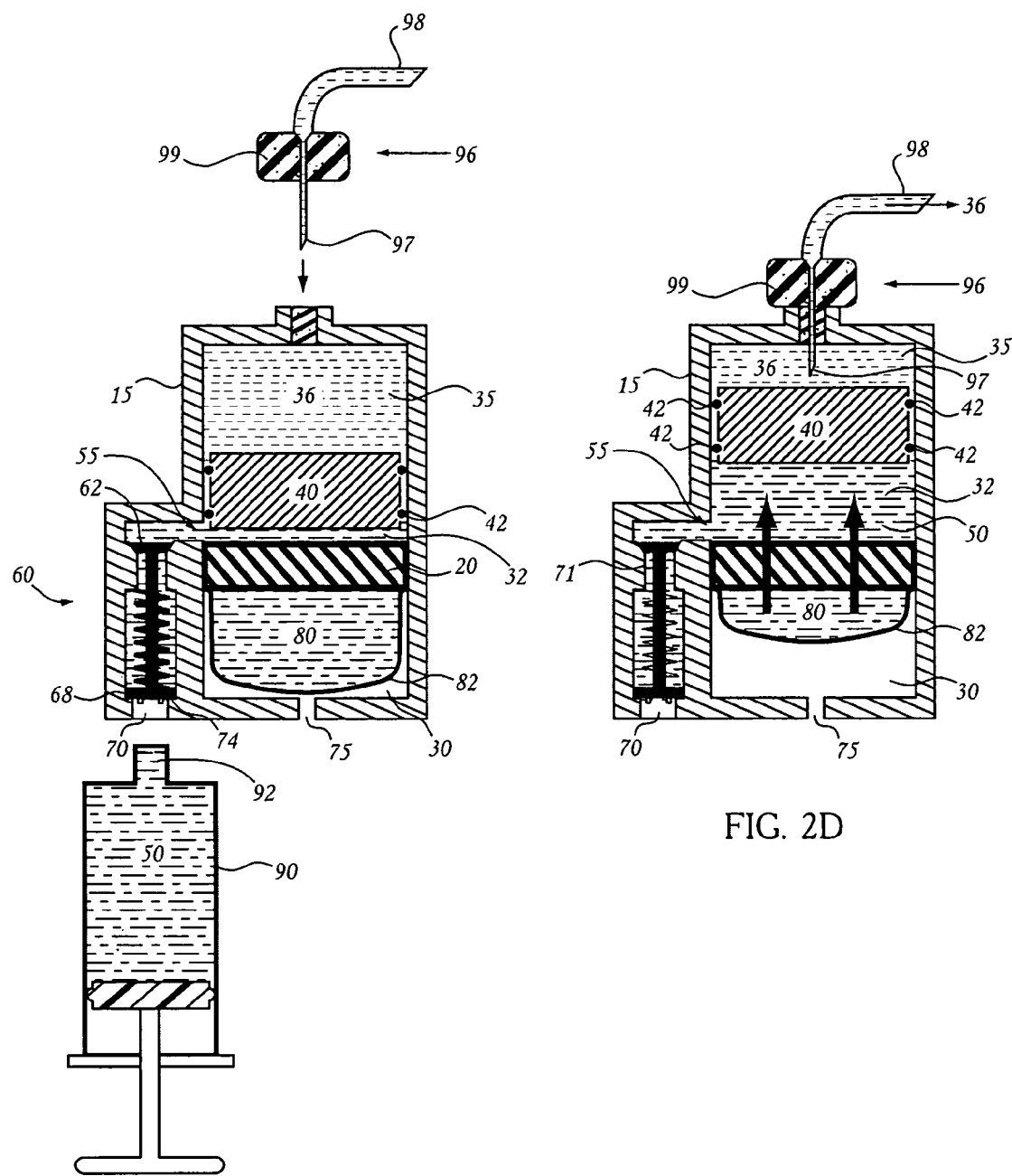

Next, as illustrated in FIG. 2C, the syringe filled with storage fluid 50 and the vial 105 are detached. When syringe tip 92 is withdrawn from opening 70, spring 66 operates to engage valve seats or discs 62, 68 with seats 72, 74 respectively to close valve 60. Alternatively instead of being a disc/seat combination, a stopper 68 may rest on ledge 74 used to oppose the action of spring 66. Delivery tubing such as an infusion set 96 or other suitable delivery set up is attached to the outlet 45 by inserting tip 97 through the outlet 45 and engaging seal 99. The septum may be pierced or a dual leur needle septum may also be used. The conduit 98 may be directed to the desired delivery location for delivery fluid 36.

The method of operating the fluid delivery system 1 to deliver fluid 36 is illustrated in FIG. 2D. Operation of the pump element 20 reduces the volume of the first chamber 30 and the third chamber 35 while increasing the volume of the second chamber 32. The moveable pump element (diaphragm 82 in the illustrated embodiment) inside the first chamber 30 contracts as electrolyte 80 moves from the pump chamber 30 through operation of the pump element 20. The increasing volume in the second chamber moves the moveable pump element 40 that in turn moves delivery fluid from the third chamber or delivery chamber through the outlet 45 to a location outside of the housing 15. Here, the delivery fluid 36 flows through the infusion set 96.

FIGS. 3A-3D illustrate the operation of a pumping system 100. The components of pumping system 100 are similar to the fluid delivery system 1 except that the first chamber 130 is adjacent the second and third chambers 132, 135 in a side-by-side or horizontal alignment system in contrast to the in-line alignment of fluid delivery system 1. Another difference is that normally closed valve, septum or flap 125 replaces valve 60 in the second chamber outlet 170. The flap 125 also illustrates how a second chamber outlet can be in line with the third and second chambers rather than in a side by side arrangement as shown in FIGS. 1A and 2A. The flow-through pump element 20 separates the first chamber 130 from the second chamber 132. The second chamber includes a conduit 110 and is separated from the third chamber 135 by the moveable pump element 40. A storage fluid 50 fills the second chamber 132 and a pump fluid 80 fills the diaphragm 80 in the first chamber.

While fluid delivery system 1 has the advantage of a small diameter and coaxial configuration, for some product applications, the height of pump system 1 may not be desired. The arrangement of the pump housing 115 in pumping system 100 results provides shorter and wider configurations that may be desired for some applications. Numerous spatial positions of the first, second and third chambers can be achieved by altering the placement of the conduit 110. Alternatively, the 110 may be a separate component inserted between the first chamber 130 and the second and third chambers 132, 135. In another alternative, the conduit 196 is formed within and is integral to a portion of the wall 194 of an embodiment of the housing 190 as shown in FIG. 3E.

FIGS. 3A-3D illustrate the operation of the pump system 100 having a first chamber 130, a second chamber 132 and a delivery chamber 135. Initially, the pumping system 100 is pre-filled with buffer 80 and storage fluid 50 and is purged of air as shown in FIG. 3A. Filling is accomplished by reducing the volume of the second chamber while increasing the volume of the delivery chamber without operation of the flow-through pump element 40 that separates the second chamber 132 from the first chamber 130. As illustrated in FIG. 3A, the syringe tip 92 lifts flap 125 (or otherwise opens a valve, seal or septum) to open a fluid pathway from outside the housing 115 to the second chamber 132 using the outlet 170. A vial 105 filled with delivery fluid 36 is attached to the opening 145 thereby placing the delivery fluid 36 in fluid communication with the delivery chamber 135.

Next, as illustrated in FIG. 3B, the syringe handle 95 is withdrawn thereby moving fluid 50 within the second chamber 132 to a location outside of the housing 115 (by way of non-limiting example, into the syringe 91 via outlet 170). Removing the storage fluid 50 from the second chamber 132 reduces the volume of the second chamber 132 and increases the volume of the delivery chamber by moving the moveable pump element 40 that separates the second chamber 132 from the delivery chamber 135. Movement of the moveable pump element 40 also pulls the delivery fluid 36 out of vial 105 through outlet 145 and into the delivery chamber 135. As shown in FIG. 3C, when filling is complete and the desired amount of delivery fluid 36 is drawn into the delivery chamber 135, the syringe 90 is withdrawn thereby closing the valve, seal or flap 125 and the vial 105 is removed. Also shown in FIG. 3C is the attachment of an infusion set 96 or other delivery device to the outlet 145. The pump system 100 is now ready for delivery.

FIG. 3D illustrates a method of operating the fluid delivery system 100 to deliver fluid 36 through outlet 145 and the attached infusion set 96. FIG. 3C illustrates the first chamber and delivery chamber volumes at the beginning of pumping. Operating the flow-through pump element 40 that separates the first chamber from the second chamber reduces the volume of the pump fluid 80 in the first chamber and the delivery fluid 35 in the delivery chamber. FIG. 3D illustrates the reduced volumes of the delivery chamber and the first chamber after pumping has commenced.

The increasing volume of pump fluid or buffer 80 in the second chamber 132 forces the moveable element 40 towards the outlet 145. Movement of the moveable element 40 towards the outlet 145 in turn reduces the volume of the delivery chamber 135 by forcing the delivery fluid 36 through the outlet 145 and hence to the delivery conduit 98.

Further improvements to handling and filling operations are illustrated in FIGS. 3E and 3F. The housing 135, portions of the first, second or third chambers may be shaped to conform to an anatomical contour. In the illustrated embodiments, a portion of the housing 135 and the first chamber 130 are contoured to provide a handhold 191. This configuration also differs from pump system 1 in that when the syringe 90 is attached to the outlet 170 the syringe 90 is axially in line with the inlet and outlet ports 145, 170. The axial alignment allows a user to curl his hand around the housing 115 from the left side (relative to the illustration) while stabilizing the drug vial 105 (or other liquid fill supply) with the thumb and index finger of the same hand. Not as shown in the illustration, but possible is for the syringe body 91 is maintained between the remaining fingers and the palm of the same hand. The syringe handle 95 can then be manipulated with the user's other hand to decrease the volume of the second chamber by drawing out the storage fluid 50 into the syringe body 91.

FIGS. 4A-4G illustrate filling, operation and features of the pump system 200. The pump system 200 includes a base member 205 that supports a first chamber 230, a second chamber 232 and a delivery chamber 235. The flow-through pump element 20 separates the first chamber 230 from the second chamber 232. The second chamber 232 includes a conduit 210 and an outlet 270. The outlet 270 provides a fluid pathway from outside the pump system to the second chamber through the base 205 as shown in FIG. 4B or through the side of housing 240 as shown in FIG. 4A. The first chamber includes a moveable pump element 282 and is filled with a suitable pump fluid or buffer 80. In this embodiment, the moveable pump element 282 is a diaphragm. The vent 275 in the first chamber aids in the movement of the moveable pump element 282. A moveable pump element 240 separates the second chamber from the delivery or third chamber. In this embodiment, the moveable pump element 240 is a diaphragm. The outlet 270 provides a fluid pathway from the third chamber to a location outside of the pump system.

FIG. 4A is a top down view of the pumping system 200 showing one possible arrangement of the first chamber 230, the delivery chamber 235 and the conduit 210 on the base 205.

Other configurations are possible such as where the walls of the pump and delivery chamber share a common wall and the conduit 210 is a passage through the common wall to place the chambers in fluid communication. The base 205 may have adhesive for skin attachment.

The first chamber is initially filled with buffer 80 and the second chamber is filled with storage fluid 50 and both chambers are purged of air as shown in FIG. 4B. The storage fluid 50 that may be the same as or different from buffer 80. The fluid 50 and buffer 80 may be an electrolyte suited to the pumping operations performed by the flow-through pump element 20.

FIGS. 4B and 4C illustrate how the volume of the second chamber 232 is reduced and the volume of the third chamber increased by drawing out buffer 50 through outlet 270 into the syringe 90. As illustrated in FIG. 4C, the syringe tip 92 lifts a flap or valve or pierces a septum (not shown but described elsewhere in this application) to establish fluid communication with the second chamber 232 via opening 270. A vial 105 filled with delivery fluid 36 is attached to the opening 270 thereby placing the delivery fluid 36 in fluid communication with the delivery chamber 235. When the syringe handle 95 is withdrawn as shown, the storage fluid 50 is removed from the second chamber 232 and draws down the diaphragm 240 and pulls the delivery fluid 36 into the delivery chamber 235. The delivery chamber volume increases and is filled with delivery fluid 36. When sufficient delivery fluid 36 has been loaded into the delivery chamber, the vial 105 and the syringe 90 are withdrawn and the outlets 270, 245 closed.

Turning now to FIGS. 4E and 4F, operation of the flow-through pump element 20 reduces the volume of the first chamber 230 and the delivery chamber 235 while increasing the volume of the second chamber 232. Operation of the flow-through pump element 20 also moves the moveable pump element 240 to deliver the delivery fluid to a location outside of the housing 238. An infusion set 96 or other delivery device (not shown but described elsewhere in this application) may be attached to the outlet 245 to direct the flow of delivery fluid.

Pump system 200 may be configured to provide a low height pumping unit. By expanding the width of the chambers along the base 205 the height of the chambers would be reduced. The reduced height may be advantageous for body-worn pumps. In some embodiments, a portion of the housing is shaped to conform to an anatomical contour. In the illustrated embodiment of FIG. 4G, the base 205 and conduit 210 may be rigidly formed into a curve or angled shape to conform to a body contour. Rather than having a fixed anatomical shape, the base 205 or other components of the pumping system 200 may be flexible. A pump having flexible components may more easily conform anatomically depending upon pump placement since the base 205, for example, may bend to conform to the user's body.

FIGS. 5A-5E are cross section views of an embodiment of a fluid delivery system 300 according to the invention. The fluid delivery system 300 is similar to the previously described fluid delivery systems and common reference numbers are used where applicable. In particular, operation of the flow-through pump element 20 reduces the volume of the first chamber 30 and third chamber 35 while increasing the volume of the second chamber 32. As before, the increasing volume of the second chamber 32 displaces the moveable pump element 40 to reduce the volume of the third chamber 35 and pump the delivery fluid 36 out of the housing 315.

The pump system 300 includes a housing 315 with first, second and third chambers, a flow-through pump element separating the first and the second chambers and moveable pump element separating the third and the second chambers. These components are contained within a single housing 315. The housing 315 includes an outlet 45 with a seal 309 preventing communication between the outlet 45 and the third chamber 35. A vent 75 and moveable pump element 82 (here, a diaphragm) are provided in the first chamber.

In addition, the pump system 300 includes an inlet 370 that provides fluid communication from outside the pump housing 315 to the conduit 318 under control of the valve 360. The conduit 318 is in fluid communication with the delivery chamber 35. The valve 360 is positioned in the housing 315 that when actuated allows communication between (1) the outlet 370 and the interior of housing 315 and (2) the first chamber 30 and the second chamber 32. A first conduit 318 provides fluid communication from outside the pump housing 315 to the third chamber 35 via outlet 370. In this illustrative embodiment, the third chamber 35 is the delivery chamber.

The valve 360 has a disc 362, stem 364, a spring 366 and a disc 368. Seats 372, 374 are formed in the wall of housing 315 and are shaped to seal with, respectively, discs 362, 368. In FIG. 5A, valve 360 is shown in the closed position where spring 366 holds discs 368, 362 in place against seats 372, 374. In this illustrative embodiment, the valve 360 is placed in the second conduit 371 to control fluid communication between the first chamber and the second chamber. The conduit 371 is formed within the wall of housing 315 and provides a fluid pathway from outlet 355 in the second chamber 32 to outlet 356 in the first chamber 30. A seal 320 around stem 364 prevents fluid from leaking out of conduit 371. When valve 360 is closed, disc 362 closes off conduit 371 thereby separating the first chamber 30 from the second chamber 32. In the illustrated embodiment, the conduits 318, 371 are both integrally formed within the housing 315. In alternative configurations, either conduit 318 or 371 may be integrally formed within the housing 315 or other external flow pathways may be provided.

Alternatively, the valve 360 may be replaced with an embodiment where a valve in the first conduit 318 that is mechanically linked to a valve in the second conduit 371. In another alternative, there is provided a dual valve comprising the valve in the first conduit 318 and the valve in the second conduit 371. In yet another alternative the valve 360 is a piston valve similar to that used in a trumpet. The piston valve has internal ports that align with the conduits 318, 371 to provide the desired fluid communication when the valve is operated. Otherwise, the ports do not align within the housing and the conduits 318, 371 are closed off.

One difference between the fluid delivery system 300 and the previously described fluid systems is the manner in which delivery fluid is loaded into the fluid delivery system. Unlike previous pump systems, the pump system 300 does not contain sufficient pump fluid or electrolyte within the first chamber for pump operation of significant duration. Instead, the pump fluid for operation of the pump is contained in the second chamber initially. However, instead of moving the fluid in the second chamber to a location outside of the housing, the fluid is instead moved to a location inside of the housing 315. In the illustrated embodiment, the fluid is moved to a location inside of the first chamber as shown in FIGS. 5B and 5C.

FIGS. 5B and 5C illustrate how pump fluid or electrolyte 80 may be moved into the first chamber 30 from the second chamber 32 as a result of loading the delivery fluid 36 into the third chamber 35. In contrast to earlier systems, the syringe 90 here is pre-filled with the desired amount of delivery fluid 36. The syringe tip 92 is inserted into opening 370 to compress spring 366 and move discs 368, 362 off of seats 374, 372, respectively as illustrated in FIG. 5B. This action opens fluid pathways from (a) outside of the housing to the third chamber and (b) between the first chamber and the second chamber. As a result, advancing handle 95 and plunger 93 forces the delivery fluid 36 through conduit 318 and into the third chamber 35. The increasing delivery fluid volume in third chamber 35 moves the moveable member 40. Movement of the moveable member 40 urges buffer 80 though the outlet 355, conduit 371 and past disc 362 through outlet 356 and into the first chamber 30. Buffer exiting outlet 356 fills and distends the diaphragm 82 as shown in FIG. 5C. In this manner a single action (by way of non-limiting example, advancing the plunger 93) ports buffer 80 from the second chamber 35 below the moveable element 40 via outlet 355 to fill diaphragm 82 while introducing a delivery fluid 36 into the third chamber 35 above the moveable element 40. One safety feature of this filling method is that the moveable element 40 is provided at the top of the third chamber 35 thereby minimizing or simplifying the removal of air trapped in chamber 35.

An additional safety feature is that, after filling, the only delivery fluid 36 in the delivery chamber is the volume provided by the pre-filled or user filled syringe as illustrated in FIG. 5B. Use of an empty third chamber 35 and pre-determined delivery volumes reduces the risk that too much delivery fluid will be placed in the delivery chamber. Another safety advantage of this method of filling is that, with the exception of the small volume of buffer 80 in diaphragm 82 initially (see FIG. 5A), the diaphragm 82 only contains as much buffer 80 as there is fluid 36 to be delivered.

This configuration may be especially advantageous if prefilled drug syringes or other pre-filled dispensers are used such as when the delivery fluid is a pharmacological agent. Utilizing pre-filled drug syringes is advantageous because it would simplify the filling procedure for the user. The user would obtain the drug in pre-filled syringes, each syringe containing exactly the volume of drug that is prescribed for that particular user. For example, one user may be prescribed 3 ml of drug to be used during a three-day period, while another user may be prescribed a volume of 1.8 ml for use over a three-day period. In each case, the user will inject the contents of the filled syringe into the delivery chamber and select a 3 day delivery cycle on user control interface 6. The user simply injects the full contents of the pre-filled syringe into the delivery chamber. This is in contrast to the fluid delivery systems 1, 100 and 200 described above where the user must monitor the amount in vial 105 or in the delivery chamber to fill the prescribed amount.

Next, as shown in FIG. 5C, handle 95 is depressed (as indicated by the arrow) forcing the delivery fluid 36 through the conduit 318 to displace the moveable pump element 40 and increase the volume of the third chamber. This movement of the moveable element 40 in turn decreases the volume of the second chamber by pushing buffer 80 out of the second delivery chamber through outlet 355 and conduit 371. The buffer 80 flows by disc 362 and then through outlet 356 to distend and fill diaphragm 82 in the first chamber 30 (by way of non-limiting example, increasing the volume of the first chamber).

Figure 5D:
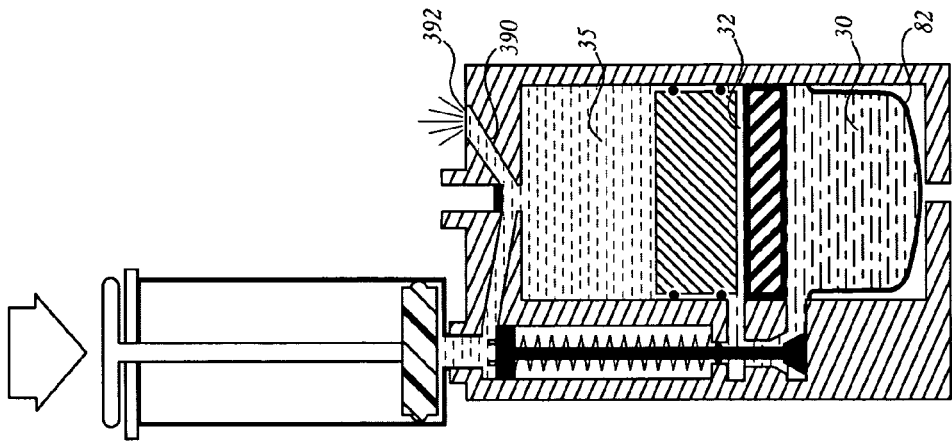
Figure 5E:
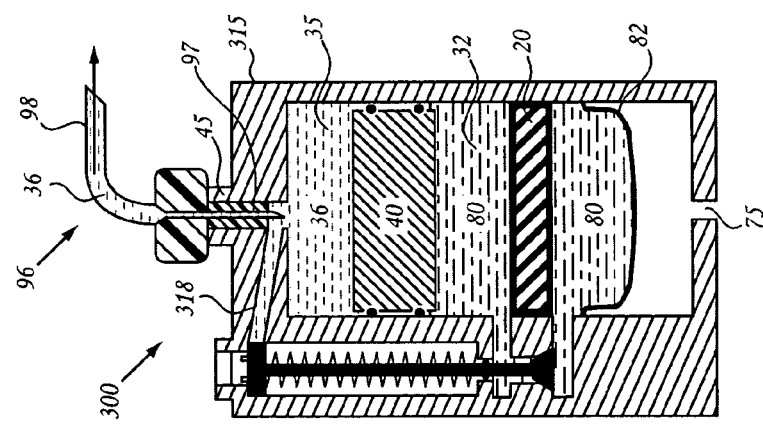

The handle 95 is advanced until all or a portion (if desired) of the delivery fluid 36 is transferred into the delivery chamber 35. When the desired amount of delivery fluid 36 is transferred into the delivery chamber, the syringe 90 is withdrawn from the opening 370 as shown in FIG. 5D. The spring 366 acts to urge discs 368, 362 to seal against seats 374, 372 to close off conduits 318, 371. FIG. 5E illustrates an infusion set 96 attached to the outlet 45. The tip 97 is used pierce the seal 309 to place the delivery chamber 35 into fluid communication with conduit 98. Other types of seals may be employed at the outlet 45, such as needle-less ports or luer-actuated ports. Because the valve 360 seals the conduit 371, operation of the pump element 20 moves buffer 80 from the first chamber 30 (within the diaphragm 82) into the second chamber 32. The increasing volume in the second chamber moves the moveable pump element 40 to decrease the volume in the third chamber that in turn pushes the delivery fluid 36 into tip 97 and hence to the conduit 98.

Figure 5F:
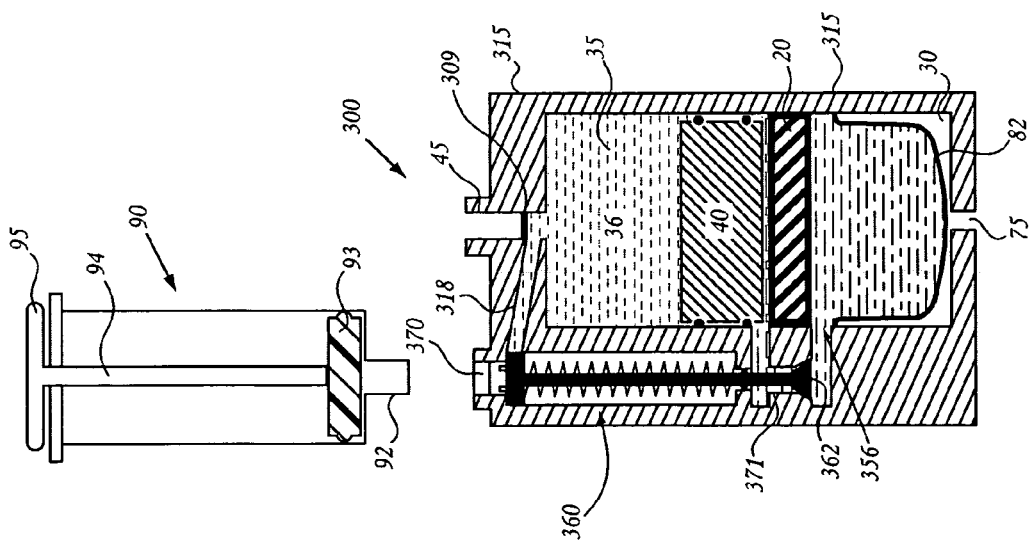

As illustrated in FIG. 5F, a hydrophobic vent 392 may also be provided in communication with the first, the second or the third chambers. The vent 392 provides an escape route for air or other gases that may be trapped in the chamber. The vent 392 may also be adapted to allow air or gases to pass but not any liquid. In the illustrative embodiment of FIG. 5F, an optional conduit 390 and vent 392 that may be included to release any air trapped during filling operations. Other configurations may also be provided with vents to purge air trapped during filling or operation. Alternatively, a valve may be used instead of a vent. Alternatively, the valve could be manually operated by the user, or automatically opened via a mechanism or an electromechanical means when a filling syringe (or other filling device) is attached. While illustrated in the context of the pump system 300, the use of additional conduits for vents with or without membranes, or valves may be applied to other configurations described herein.

FIGS. 6A-6F illustrate an embodiment of pump system 600 according to the invention. The pump system 600 includes a first chamber 630 separated from a second chamber 632 by a flow-through pump element 620. The flow-through pump element 620, contained within housing 618, is configured in this embodiment as an electrokinetic pump having electrodes 624 on either side of a dielectric element 622 as described above in FIG. 1B. The second chamber 632 has an outlet 670 and is separated from the third chamber 635 by a moveable pump element 640. The third chamber has an outlet 645. In the illustrated embodiment, the moveable pump elements 640, 680 are diaphragms, however, other forms of moveable pump elements may be used as described herein.

The first, second and third chambers are formed by a plurality of cells 615 arranged on a base 605. The cells 615 have a housing 610 containing a moveable pump element 680, 640. A plurality of conduits 612 provide fluid communication between cells 615. The conduits 612 may have variable lengths and allow for the footprint of the base 605 to be varied. The position and configuration of the components of pump system 600 to be varied by adjusting the geometry of the conduits 612, the dimension of the cells 615 and the manner by which the conduits 612 connect the cells 615.

FIGS. 6A and 6B illustrate, respectively, top and side views, of the pump system 600 prior to filling the third chamber with delivery fluid. In this condition, the first chamber and the second chamber are filled with fluid. The first chamber is filled with a pump fluid, such an electrolyte or other fluid suited to the type of pump being used. The pump fluid is within the moveable pump element 680 inside of housing 610. The second chamber optionally is filled with a storage fluid that is within a moveable pump element 640 within the housing 610. A syringe 92 is attached to the outlet 670 that provides a fluid path to the second chamber.

FIGS. 6C and 6D illustrate, respectively, top and side views of the pump system 600 during filling operations. A drug vial is attached to the outlet 645 and in communication with the third chamber 635. Using the syringe 92, the volume of the second chamber is reduced by removing the storage fluid 80 from the second chamber and into the syringe 92. At the same, the changing volume of the second chamber moves the moveable pump element 640 between the second and third chambers to increase the volume of the third chamber as it is filled with delivery fluid from the vial.

FIGS. 6E and 6F illustrate, respectively, top and side views of the pump system 600 during delivery operations. Operation of the pump element 620 moves pump fluid from the first chamber 630 through the pump element 620 into and increasing the volume of the second chamber 632. The increasing volume of the second chamber displaces the moveable pump element 640 to decrease the volume of the third chamber by moving delivery fluid out through outlet 645 and an infusion set or the like attached to outlet 645.

FIGS. 7A-7E illustrate cross section views of a pump system 700 according to one embodiment of the present invention. Pump system 700 is configured similar to pump system 100 in FIG. 3. Pump system 700 differs from pump system 100 in that the second chamber is not filled with storage solution. One reason to provide the storage solution in the first and second chambers is to ensure that the flow-through pump element 20 remains in the proper environment to begin operation when the pump system is placed in service. In the case of an electrokinetic pump, the pump element 20 would be best stored with electrolyte one both sides of and filling the pump. Pump system 700 solves this problem by dividing the second pump chamber into two parts separated by a seal 705. One part of the second chamber is between the pump element 20 and the seal 705 and is filled with a suitable pump fluid. The other part of the second chamber is from the seal 705 to the moveable pump element 41. The moveable pump element 41 separates the second chamber from the third chamber. The moveable pump element 41 is divided into two parts, the first portion 41A and the second portion 41B. A fluid 55 separates the first portion from the second portion.

FIGS. 7A and 7B provide alterative initial positions prior to filling the third chamber 135. In FIG. 7B, the moveable pump element 41 is positioned such that the third chamber volume is larger than the second chamber volume. This placement of the moveable pump element 41 more readily allows the practice of the drug aspiration technique of initially injecting air into the vial attached to the outlet 145. Additionally, the placement illustrated in FIG. 7B allows one of the moveable pump element portions to be placed against and reinforce the seal 705. The handle 95 may optionally be disconnected (by way of non-limiting example, unscrew at threaded connection 792) during shipping and attached prior to filling the third chamber. In the configuration illustrated in FIG. 7A, the moveable pump element 41 is positioned such that the second chamber volume is greater than the third chamber volume.

After attaching a vial or other storage container to the outlet 145, the third chamber volume is increased and the second chamber volume decreased by withdrawing the moveable element 41 within the second chamber. The movement of the moveable pump element 41 increases the volume of the third chamber. By pulling the handle until the moveable pump element reaches the housing (by way of non-limiting example, the maximum volume for the third chamber) the fluid separating the first and second moveable pump element portions 41A, 41B aligns with seal 705. Thereafter, the handle 95 may be removed. Operation of the flow though pump element 20 ruptures the seal 705 as shown in FIG. 7D. Continued pump operation reduces the volume of the first chamber and increases the volume of the second chamber by advancing one portion of the moveable pump element 41. Operation of the flow-through pump element 20 separates the moveable pump element 41 positioned between the second chamber and the third chamber. In the illustrated embodiment, moveable pump element portion 41A moves to reduce the volume of the third chamber and dispense the delivery fluid through outlet 145.

Figure 8:
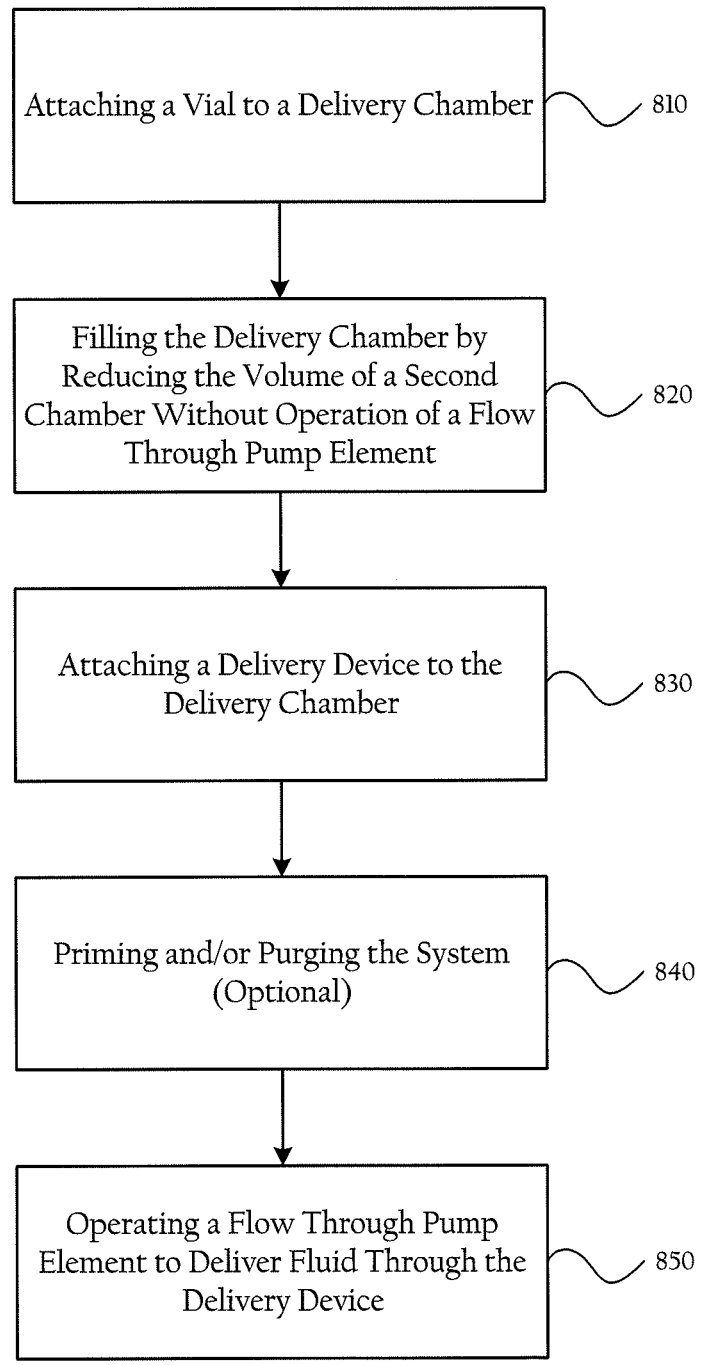
FIG. 8 illustrates a method of fluid delivery.

FIG. 8 illustrates a flow chart 800 depicting an exemplary fluid delivery method. First, at step 810, attach a vial to a delivery chamber. By way of non-limiting examples, this step is illustrated and described with regard to FIGS. 2A, 3A, 3F, 4C, 6C and 7C. Next, at step 820, is the step of filling the delivery chamber by reducing the volume of a second chamber without operation of a flow-through pump element. By way of non-limiting examples, this step is illustrated and described with regard to FIGS. 2B, 3B, 4C, and 5C. The step, step 830, is the step of attaching a delivery device to the delivery chamber. By way of non-limiting examples, this step is illustrated and described with regard to FIGS. 2C, 3C, and 5E. Optionally, before or after attaching the delivery device, the system may be primed or purged (step 840). Finally, step 850, the step of operating a flow through pump element to deliver fluid through the delivery device. By way of non-limiting examples, this step is illustrated and described with regard to FIGS. 1A, 2D, 3D, and 5E.

The foregoing illustrative embodiments have used certain terms to provide an explanation of the principal involved or operation of the illustrated system. It is to be appreciated that numerous alternatives for components and elements are possible. For example, the pump element may be an electrokinetic pump but pump element also includes the use of diaphragm pumps, piston pumps, and piezoelectric pumps. The supporting electronics 5 and electrical connectors 26 would be modified as needed according to the type of pump element used. Additionally, many of the illustrative configurations described the use of a movable pump element. It is to be appreciated that the movable pump element may be a piston or a diaphragm and that both may be used in a single system (by way of non-limiting example, as illustrated in FIG. 1A). The diaphragm may be a 'rolling' type diaphragm. Rolling diaphragms have a convolute that allows predictable travel of the diaphragm. While a rolling diaphragm does have advantages, the invention is not so limited and other types of diaphragms and moveable pump elements may be used. Other types of deformable barriers such as bellows may be used.

The process of drug aspirating and air purging has been shortened in many of the illustrative descriptions. For configurations describing filling the pump with delivery fluid, the description simply indicates to pull back on a handle or pump housing to drawn drug or delivery fluid in. Those of ordinary skill will appreciate that this is an abbreviated instruction. Like any drug aspiration process, trapped air is vented before the drug is delivered. As such, the full process includes draw drug in by pulling back on the handle or housing, then while holding the unit with the drug exit port at the top, flick the unit to release bubbles, and then press the syringe handle in to purge air out of the unit. The process is repeated if necessary until all visible air is removed and the unit is filled with the desired amount of drug. This process is identical to the typical method used by medical practitioners to aspirate drug into syringes and purge air. Alternatively, a step of injecting air into the vial may be included.

A generic infusion set 96 is described and many of the pump system embodiments are represented as connected to an infusion set. While not illustrated in every embodiment, a similar configuration of an infusion set connection or other suitable delivery device can be inferred for all pump system embodiments. Alternatively, the delivery fluid 36 or drug may be dispensed without an infusion set such as, for example, when it is delivered directly into a canula or elsewhere.

The use of liquid and/or air seals have been illustrated in some embodiments. In some embodiments, those components requiring seals (pistons, etc.) have two o-ring seals (by way of non-limiting example, seals 42) however, in some other embodiments, only a single o-ring seal is used. Two seals are typically used in medical syringes and have thus been shown in pairs on most of the pistons described herein. It is to be appreciated that one or more o-rings may be used, however, or alternate types of seals may be employed. 0-rings may be made from conventional sealing materials suited to medical application such as silicone and urathane, for example.

Many of the configurations may be partially filled with drug or delivery fluid to any desired amount. Additionally, in some embodiments, the portion of pump housing that stores the delivery fluid would be transparent and graduated to allow visibility and amount of the delivery fluid 36 present. In addition, a transparent housing would also allow visibility of any air that needs to be purged during the filling process. Volumetric increment markings may also be appropriately provided on the pump housing by printing, stamping, embossing, painting or otherwise indicating the contents of the delivery fluid 36 within a drug chamber.

One benefit of the pumping systems described herein is that these systems provide indirect pumping of delivered liquids regardless of the type of pump used for pump element 20. As the descriptions above make clear, the delivery fluid 36 does not pass through any pump mechanism. In fact, operation of the pump element is unnecessary to fill the pump housing with delivery fluid. Another advantage is the decreased likelihood of damage to fluids that are susceptible to mechanical and/or chemical degradation such as long chain protein molecules and peptides. Mechanical actions including compression, shearing, and extrusion, as well as exposure to electrical currents can cause molecular level damage to some fluids. By obviating the need for the fluids to pass through the pump mechanism, concern over pumping damage to these compounds is diminished.

The term buffer has been used throughout the description. Buffer refers to any suitable working fluid that may be used by a particular pumping system. In many pumping system embodiments, the buffer or working fluid is any fluid having a viscosity low enough to be pumped through the pump element. In those embodiments where the pump element is an electrokinetic pump, working fluid is an electrolyte suited to the specific electrodes and dielectric material used by the electrokinetic pump. In one specific embodiment, the electrolyte is a buffered electrolyte. One buffered electrolyte is a buffer made from TRIS [tris (hydroxymethyl) aminomethane] and sorbic acid at a concentration of 10 Mm and a pH of 8.3. Other common buffer ions work as well. For example, TRIS-HCL, borate or sodium acetate buffers can be used. The buffer may also include other additives such as preservatives.

The term delivery fluid has been used throughout the description. In many pumping system embodiments, the delivery fluid is any fluid having a viscosity low enough to be pumped through action of the pump element. In some embodiments, the delivery fluid is a pharmacological agent. In other embodiments, the delivery fluid is a therapeutic agent. In still other embodiments, the delivery fluid is a saline solution or Ringers solution.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. In addition, the intended uses of the present invention include a variety of medical applications as well as other applications where highly precise, compact devices for fluid transport are needed. It should be understood that various alternatives to these embodiments of the invention described herein may be employed in practicing the invention. It is intended at the following claims defined the scope of the invention and it methods and structures within the scope of these claims and their equivalents be covered thereby.

What is claimed is:

1. A fluid delivery system, comprising:
a housing having a first chamber, a second chamber and a third chamber;
an electrokinetic pump element separating the first chamber from the second chamber, the electrokinetic pump element comprising a porous dielectric material disposed between a pair of electrodes;
a first moveable pump element separating the second chamber from the third chamber;
a second moveable pump element defining a wall of the first chamber;
a pump liquid in the first chamber;
a storage liquid in the second chamber in contact with the flow-through pump element;
a first outlet through a wall in the housing in communication with the third chamber; and a second outlet through a wall in the housing at the second chamber, the second outlet configured to allow the storage liquid in the second chamber to flow therethrough without flowing through the electrokinetic pump element as the first movable element moves towards the second chamber.

2. The fluid delivery system according to claim 1 wherein the second moveable pump element is a diaphragm.

3. The fluid delivery system according to claim 1 further comprising: a valve separating the second outlet from an exterior of the housing.

4. The fluid delivery system according to claim 1 further comprising: a flap separating the second outlet from an exterior of the housing.

5. The fluid delivery system according to claim 1 further comprising: a valve positioned in the housing that when actuated allows communication between the third chamber and an exterior of the housing and communication between the second chamber and the first chamber.

6. The fluid delivery system according to claim 1 further comprising an air vent in communication with the first chamber, the second chamber or the third chamber.

7. The fluid delivery system according to claim 1 wherein a portion of the housing is shaped to conform to an anatomical contour.

8. The fluid delivery system of claim 1, wherein the fluid delivery system is configured such that a volume of the second chamber reduces and a volume of the third chamber increases during removal of the storage fluid from the second chamber.

9. The fluid delivery system of claim 1, wherein the fluid delivery system is configured such that a delivery fluid can be filled into the third chamber while storage liquid is removed from the second chamber.

10. The fluid delivery system of claim 9, wherein the fluid delivery system is further configured such that, in operation, the electrokinetic pump element is configured to move the pump fluid from the first chamber and into the second chamber, thereby causing the delivery fluid to be expelled out of the first outlet.

11. The fluid delivery system of claim 1, wherein the storage liquid is a different fluid than the pump liquid.

12. The fluid delivery system of claim 1, wherein the storage liquid and the pump liquid comprise the same fluid.

13. The fluid delivery system of claim 1, wherein the pump liquid is an electrolyte.

14. The fluid delivery system of claim 1, wherein the second moveable pump element is within the housing.

* * * * *